US008795893B2

(12) United States Patent
Ogihara

(10) Patent No.: US 8,795,893 B2
(45) Date of Patent: *Aug. 5, 2014

(54) NONAQUEOUS SECONDARY BATTERY ELECTRODE, NONAQUEOUS SECONDARY BATTERY INCLUDING THE SAME, AND ASSEMBLED BATTERY

(75) Inventor: Nobuhiro Ogihara, Nagakute (JP)

(73) Assignee: Kabushiki Kaisha Toyota Chuo Kenkyusho, Nagakute-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/814,703

(22) PCT Filed: Oct. 19, 2011

(86) PCT No.: PCT/JP2011/074054
§ 371 (c)(1),
(2), (4) Date: Feb. 6, 2013

(87) PCT Pub. No.: WO2012/053553
PCT Pub. Date: Apr. 26, 2012

(65) Prior Publication Data
US 2013/0136972 A1 May 30, 2013

(30) Foreign Application Priority Data

Oct. 21, 2010 (JP) .................................. 2010-236765
May 23, 2011 (JP) .................................. 2011-115093

(51) Int. Cl.
| | | |
|---|---|---|
| *H01M 4/13* | (2010.01) | |
| *H01M 4/66* | (2006.01) | |
| *C07C 63/38* | (2006.01) | |
| *H01M 4/60* | (2006.01) | |
| *H01M 10/0569* | (2010.01) | |
| *H01M 4/38* | (2006.01) | |
| *C07C 63/333* | (2006.01) | |
| *H01M 2/10* | (2006.01) | |
| *C07C 63/46* | (2006.01) | |
| *H01M 4/36* | (2006.01) | |

(52) U.S. Cl.
CPC ................ *H01M 4/606* (2013.01); *Y02E 60/12* (2013.01); *H01M 4/366* (2013.01); *H01M 4/661* (2013.01); *C07C 63/38* (2013.01); *H01M 10/0569* (2013.01); *H01M 4/381* (2013.01); *C07C 63/333* (2013.01); *H01M 2/1016* (2013.01); *H01M 4/60* (2013.01); *C07C 63/46* (2013.01)
USPC ........................................ 429/218.1; 429/213

(58) Field of Classification Search
None
See application file for complete search history.

(56) References Cited

U.S. PATENT DOCUMENTS 5,529,859 A * 6/1996 Shu et al. ...................... 429/331
(Continued)

FOREIGN PATENT DOCUMENTS

JP     A-2004-111374     4/2004
(Continued)

OTHER PUBLICATIONS

Banerjee et al. (Cryst. Growth Des. 9 (2009) 2500-2503).*
(Continued)

*Primary Examiner* — Ula C Ruddock
*Assistant Examiner* — Lisa S Park Gehrke
(74) *Attorney, Agent, or Firm* — Oliff PLC

(57) ABSTRACT

A nonaqueous secondary battery electrode contains, as an electrode active material, a layered composition including organic backbone layers containing an aromatic compound that is a dicarboxylic acid anion having two or more aromatic ring structures and having the two carboxylic acid anions of the dicarboxylic acid anion bonded to diagonally opposite positions of the aromatic compound and alkali metal element layers containing an alkali metal element coordinated to oxygen contained in the carboxylic acid anion to form a backbone. The nonaqueous secondary battery electrode is preferably used as a negative electrode. In addition, the layered composition is preferably formed in layers by π-electron interaction of the aromatic compound and has a monoclinic crystal structure belonging to the space group $P2_1/c$.

19 Claims, 10 Drawing Sheets

(56) References Cited

U.S. PATENT DOCUMENTS

| | | | |
|---|---|---|---|
| 7,476,463 B2* | 1/2009 | Desilvestro et al. | 429/152 |
| 2007/0065719 A1 | 3/2007 | Timonov et al. | |
| 2007/0292760 A1* | 12/2007 | Patoux et al. | 429/223 |
| 2008/0090149 A1 | 4/2008 | Sano et al. | |
| 2010/0233534 A1* | 9/2010 | Iwama et al. | 429/209 |
| 2011/0287317 A1 | 11/2011 | Nakanishi | |

FOREIGN PATENT DOCUMENTS

| | | |
|---|---|---|
| JP | A-2004-342605 | 12/2004 |
| JP | A-2007-508709 | 4/2007 |
| JP | A-2008-287976 | 11/2008 |
| JP | A-2009-021229 | 1/2009 |
| JP | A-2009-037868 | 2/2009 |
| JP | A-2009-187940 | 8/2009 |
| JP | A-2010-113870 | 5/2010 |
| JP | A-2010-118320 | 5/2010 |
| WO | WO 2005/036572 A1 | 4/2005 |

OTHER PUBLICATIONS

Tarascon et al. (Nature Materials 8 (2009) 120-125).*
Banerjee et al. (Cryst. Growth Des. 11 (2011) 4704-4720).*
Kaduk (Acta Cryst. B56 (2000) 474-485).*
Banerjee et al. (Cryst. Growth Des. 9 (2009) 4922-4926).*
International Search Report dated Jan. 17, 2012 for International Patent Application No. PCT/JP2011/074054 (with translation).
Nature Materials, "Conjugated dicarboxylate anodes for Li-ion batteries", M. Armand et al., vol. 8, Feb. 2009, pp. 120-125.
Nature Materials, "High rate capabilities $Fe_3O_4$-based Cu nano-architectured electrodes for lithium-ion battery applications", P.L. Taberna et al., vol. 5, Jul. 2006, pp. 567-573.
Journal of Power Sources, "MnO/C core-shell nanorods as high capacity anode materials for lithium-ion batteries", Bing Sun et al., vol. 196, 2011, pp. 3346-3349.
Electrochemistry Communications, "Electrochemically deposited nanowires of manganese oxide as an anode material for lithium-ion batteries", Mao-Sung Wu et al., vol. 8, 2006, pp. 383-388.
U.S. Appl. No. 13/439,377 in the name of Ogihara filed Apr. 4, 2012.
U.S. Appl. No. 13/856,776 in the name of Ogihara et al. filed Apr. 4, 2013.
Aug. 27, 2013 Office Action issued in U.S. Appl. No. 13/439,377.
Jan. 2, 2014 Office Action issued in U.S. Appl. No. 13/439,377.

* cited by examiner

NONAQUEOUS SECONDARY BATTERY ELECTRODE, NONAQUEOUS SECONDARY BATTERY INCLUDING THE SAME, AND ASSEMBLED BATTERY

TECHNICAL FIELD

The present invention relates to nonaqueous secondary battery electrodes, nonaqueous secondary batteries including the nonaqueous secondary battery electrodes, and assembled batteries.

BACKGROUND ART

Recently, the widespread use of hybrid cars, which can be driven by the energy of both gasoline and electricity, and devices requiring power supplies, such as uninterruptible power supplies, mobile communications devices, and portable electronic devices, has created an enormous need for improvements in the performance of rechargeable storage devices used therefor as power supplies. Specifically, there is a need for improved properties such as increased power, capacity, and cycle life.

To provide storage devices with such properties, research has been directed to the use of organic compounds as electrode active materials. Recently, organic compounds having a π-electron conjugated cloud have been suggested as novel active materials capable of absorbing and releasing lithium, which has the potential for high-speed charge and discharge (see, for example, Patent Documents 1 and 2). Also suggested is a lithium-dicarboxylate containing conjugated organic active material having an organic backbone composed of dilithium trans-muconate or dilithium terephthalate (see, for example, Non-Patent Document 1). This active material is characterized in that its organic backbone has a conjugated structure, which allows oxidation and reduction (absorption and release of lithium).

Also suggested are negative electrodes based on the conversion reaction of a metal oxide (e.g., MOx, where M is Fe, Co, Ni, Cu, Mn, or the like) such as manganese oxide or iron oxide (see, for example, Non-Patent Documents 2 to 4). These negative electrodes are charged and discharged by the reaction formula $MOx + xe^- + 2xLi^+ \rightarrow M + xLi_2O$.

[Patent Document 1] JP 2004-111374 A
[Patent Document 2] JP 2004-342605 A
[Non-Patent Document 1] Nature Material, Vol. 8, 120-125 (2009)
[Non-Patent Document 2] Nature Material, Vol. 5, 567-573 (2006)
[Non-Patent Document 3] J. Power Sources., 196, 3346-3349(2011)
[Non-Patent Document 4] Electrochm. Commu., 8, 383-388 (2006)

DISCLOSURE OF INVENTION

The batteries in Patent Documents 1 and 2 described above, however, operate at a potential of 2.8 to 3.7 V with respect to lithium metal, meaning that they have insufficient energy densities. The battery in Non-Patent Document 1 has a conjugated structure that allows absorption and release of lithium, although the charge-discharge capacity thereof is insufficient, and there is a need for improved charge-discharge properties. Typical negative electrode materials used for lithium batteries are currently carbon materials such as graphite, which allow a redox reaction to occur at about 50 mV with respect to metallic lithium. This potential is close to that of metallic lithium, and there is a need for a secondary battery that has a sufficiently higher potential than lithium metal and that can itself operate at a higher voltage.

For negative electrodes based on conversion reaction, the lithium absorption reaction, which corresponds to the charge reaction at the negative electrode, occurs at a potential of 0.5 to 1.0 V with respect to metallic lithium, although the lithium release potential, which corresponds to the discharge reaction at the negative electrode, occurs at a potential of 1.5 to 2.0 V with respect to metallic lithium; thus, the negative electrode is considerably polarized. When used as a negative electrode, therefore, electrodes based on conversion reaction cause a problem in that the battery voltage drops during discharge.

In view of the foregoing problems, a primary object of the present invention is to provide a nonaqueous secondary battery electrode with improved charge-discharge properties and a nonaqueous secondary battery including such a nonaqueous secondary battery electrode.

After extensive research in order to achieve the above object, the inventors have found that a composition prepared using an aromatic compound that is a dicarboxylic acid anion by allowing lithium to coordinate to oxygen contained in the carboxylic acid has improved charge-discharge properties with chemical stability and a suitable potential with respect to lithium metal, thus completing the present invention.

Specifically, a nonaqueous secondary battery electrode of the present invention contains, as an electrode active material, a layered composition including organic backbone layers containing an aromatic compound that is a dicarboxylic acid anion having two or more aromatic ring structures and alkali metal element layers containing an alkali metal element coordinated to oxygen contained in the carboxylic acid anion to form a backbone.

A nonaqueous secondary battery of the present invention includes the nonaqueous secondary battery electrode described above and an ion-conducting medium that conducts alkali metal ions.

In addition, a nonaqueous secondary battery electrode of the present invention may include a positive electrode mixture containing a positive electrode active material that absorbs and releases an alkali metal; a negative electrode mixture containing the layered composition as a negative electrode active material that absorbs and releases the alkali metal; and a collector having the positive electrode mixture provided on one side thereof and the negative electrode mixture provided on the other side thereof and formed of a collector metal that dissolves at a potential lower than the redox potential of the positive electrode active material and that undergoes an alloying reaction with the alkali metal at a potential higher than the redox potential of the negative electrode active material.

In addition, a nonaqueous secondary battery of the present invention includes any one of the nonaqueous secondary battery electrodes described above and an ion-conducting medium that conducts alkali metal ions, and the ion-conducting medium may contain a halogenated carbonate.

An assembled battery of the present invention includes a plurality of connected nonaqueous secondary batteries, each including the above nonaqueous secondary battery electrode including the collector metal and an ion-conducting medium that conducts alkali metal ions.

The nonaqueous secondary battery electrodes and nonaqueous secondary batteries of the present invention provide improved charge-discharge properties. Although not fully understood, it is believed that this advantage is provided for the following reason. For example, the layered composition, serving as an active material, has four coordination bonds between the oxygen in the dicarboxylic acid and the alkali metal element (e.g., lithium), which presumably makes it insoluble in the nonaqueous electrolyte solution to maintain its crystal structure, thus improving the stability of the charge-discharge cyclability. In the layered composition, the organic backbone layers presumably function as redox sites, whereas the alkali metal element layers presumably function as alkali-metal-ion absorbing sites responsible for charge and discharge. In addition, for example, in the case of a negative electrode active material for a nonaqueous secondary battery that uses lithium ions, the electrode of the present invention has a charge-discharge potential of 0.5 to 1.0 V with respect to lithium metal, which prevents a significant decrease in energy density due to a decrease in the operating voltage of the battery and also prevents precipitation of lithium metal around 0 V with respect to lithium metal. This novel layered composition (crystalline organic-inorganic composite material) presumably improves the charge-discharge properties.

In addition, in the nonaqueous secondary battery electrode containing the layered composition as an electrode active material and including a collector formed of a collector metal that dissolves at a potential lower than the redox potential of the positive electrode active material and that undergoes an alloying reaction with the alkali metal at a potential higher than the redox potential of the negative electrode active material, and also in the assembled battery, the positive electrode mixture and the negative electrode mixture can be provided on either side of the collector because little alloying reaction occurs between the collector metal and the alkali metal. This allows efficient connection of a plurality of nonaqueous secondary batteries including an ion-conducting medium that conducts alkali metal ions and a nonaqueous secondary battery electrode including a collector metal. Thus, a nonaqueous secondary battery having high energy density can be provided.

In addition, the nonaqueous secondary battery including a nonaqueous secondary battery electrode containing the layered composition as an electrode active material and an ion-conducting medium containing a halogenated carbonate provides improved charge-discharge cyclability. Although not fully understood, it is believed that this advantage is provided for the following reason. For example, during initial absorption of alkali metal ions into the layered composition, which serves as an electrode active material, the halogenated carbonate is probably reduced to form an alkali halide (e.g., lithium fluoride), which exhibits a strong intermolecular interaction with the carboxylic acid groups of the layered composition to stabilize the interface of the electrode active material.

BEST MODES FOR CARRYING OUT THE INVENTION

A nonaqueous secondary battery of the present invention includes a positive electrode containing a positive electrode active material that absorbs and releases an alkali metal, a negative electrode containing a negative electrode active material that absorbs and releases the alkali metal, and an ion-conducting medium that is disposed between the positive electrode and the negative electrode and that conducts alkali ions. The nonaqueous secondary battery of the present invention contains a layered composition of the present invention as at least one of positive and negative electrode active materials. The layered composition of the present invention includes organic backbone layers containing an aromatic compound that is a dicarboxylic acid anion having two or more aromatic ring structures and alkali metal element layers containing an alkali metal element coordinated to oxygen contained in the carboxylic acid anion to form a backbone. The layered composition of the present invention is preferably a negative electrode active material. In addition, the alkali metal contained in the alkali metal element layers may be, for example, one or more of Li, Na, K, and the like, preferably Li. In addition, the alkali metal that is absorbed and released during charge and discharge may be the same as or different from the alkali metal element contained in the alkali metal element layers, for example, one or more of Li, Na, K, and the like. For illustration purposes, a nonaqueous secondary battery that uses the layered composition as a negative electrode active material, Li as the alkali metal contained in the alkali metal element layers, and Li as the alkali metal that is absorbed and released during charge and discharge will be mainly described below.

Figure 1:
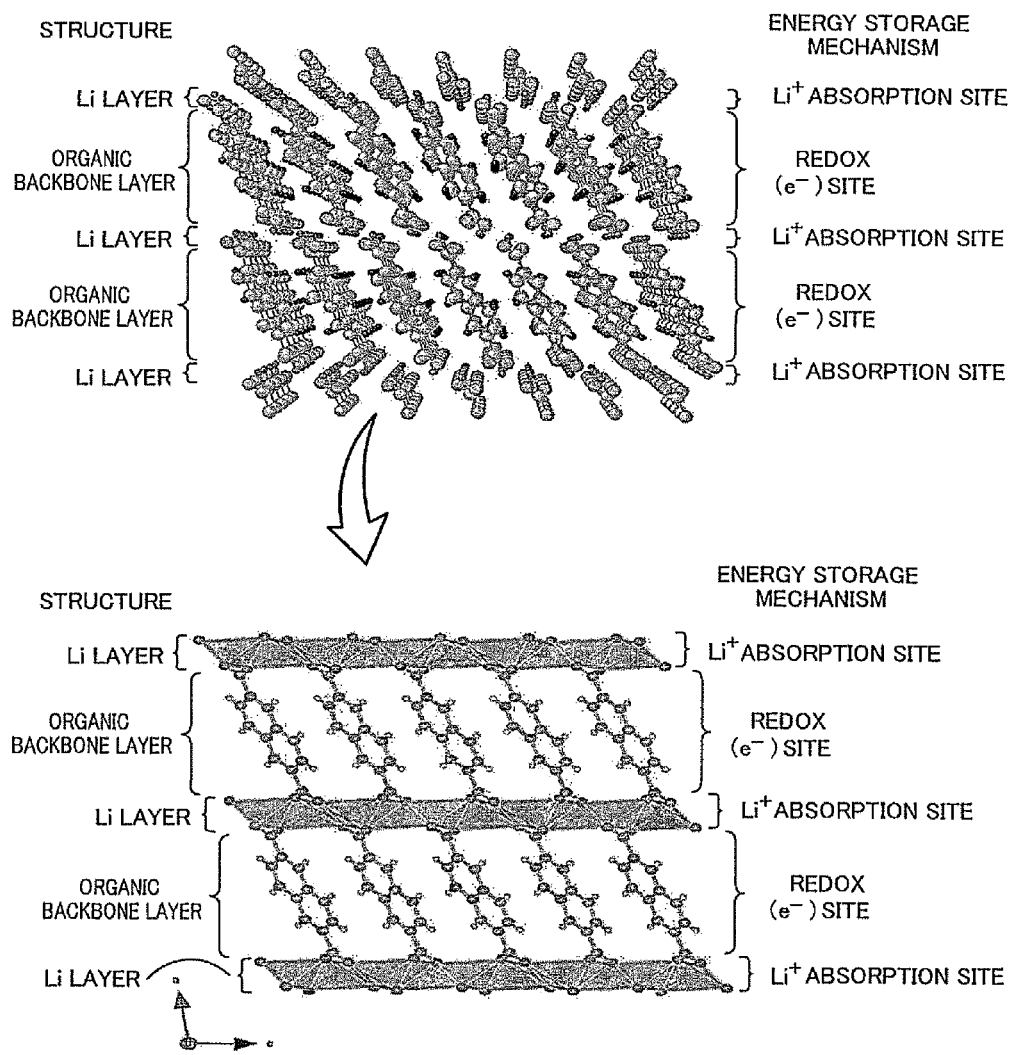
FIG. 1 is an illustration showing an example of the structure of a layered composition of the present invention.

The negative electrode of the present invention contains the layered composition as a negative electrode active material. FIG. 1 is an illustration showing an example of the structure of the layered composition of the present invention. This layered composition includes organic backbone layers and alkali metal element layers. For higher structural stability, the layered composition is preferably formed in layers by π-electron interaction of the aromatic compound and has a monoclinic crystal structure belonging to the space group $P2_1/c$. For higher structural stability, additionally, the layered composition preferably has formula (1), where four oxygen atoms from different dicarboxylic acid anions form four coordination bonds with the alkali metal element. In formula (1), each R has two or more aromatic ring structures, and two or more of Rs may be the same, or one or more of Rs may be different. In addition, A is an alkali metal element. Thus, the layered composition preferably has a structure in which the organic backbone layers are joined by the alkali metal element.

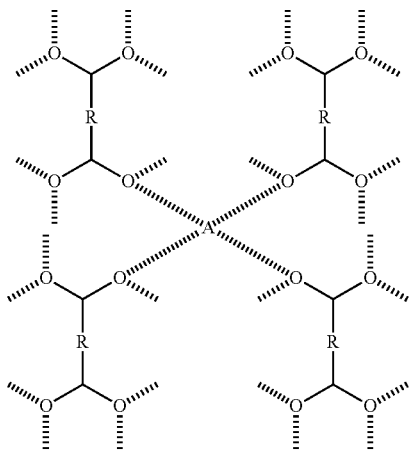

Formula (1)

where each R has two or more aromatic ring structures, and two or more of Rs may be the same, or one or more of Rs may be different. A is an alkali metal element.

The organic backbone layers contain an aromatic compound that is a dicarboxylic acid anion having two or more aromatic ring structures. The two or more aromatic ring structures may be, for example, an aromatic polycyclic compound, such as biphenyl, that includes two or more linked aromatic rings, or a fused polycyclic compound, such as naphthalene, anthracene, or pyrene, that includes two or more fused aromatic rings. These aromatic rings may be five-, six-, or eight-membered rings, preferably six-membered rings. In addition, the aromatic compound preferably has two to five aromatic rings. An aromatic compound having two or more aromatic rings easily forms a layered structure, and an aromatic compound having five or less aromatic rings has a higher energy density. The aromatic compound contained in the organic backbone layers preferably has the two carboxylic acid anions of the dicarboxylic acid anion bonded to diagonally opposite positions of the aromatic ring structures. This facilitates formation of the layered structure of the organic backbone layers and the alkali metal element layers. The diagonally opposite positions to which the carboxylic acids are bonded may be the positions where the two carboxylic acids are farthest from each other, for example, the 2- and 6-positions if the aromatic ring structures are naphthalene, and the 2- and 7-positions if the aromatic ring structures are pyrene. The aromatic compound contained in the organic backbone layers may have a structure represented by general formula (2), where R may be the above aromatic ring structure having two or more aromatic ring structures. Specifically, the aromatic compound contained in the organic backbone layers may be one or more of aromatic compounds of formulas (3) to (5). Preferably, in formulas (3) to (5), n is an integer of 2 to 5, and m is an integer of 0 to 3. If n is 2 to 5, the organic backbone layers have a suitable size, thus providing a higher charge-discharge capacity. If m is 0 to 3, the organic backbone layers have a suitable size, thus providing a higher charge-discharge capacity. The aromatic compounds of formulas (3) to (5) may have a substituent or a heteroatom in the structures thereof. Specifically, the hydrogen in the aromatic compound may be replaced by halogen, linear or cyclic alkyl, aryl, alkenyl, alkoxy, aryloxy, sulfonyl, amino, cyano, carbonyl, acyl, amide, or hydroxy as a substituent, and the carbon in the aromatic compound may be replaced by nitrogen, sulfur, or oxygen.

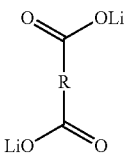

Formula (2)

where R has two or more aromatic ring structures.

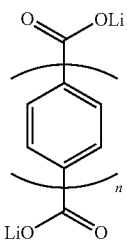

Formula (3)

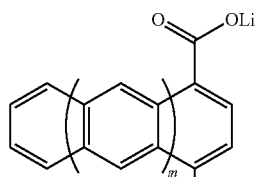

Formula (4)

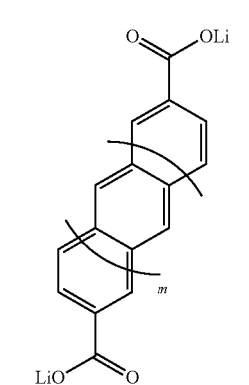

Formula (5)

where n is an integer of 2 to 5, m is an integer of 0 to 3, and the aromatic compounds may have a substituent or a heteroatom in the structures thereof.

As shown in FIG. 1, the alkali metal element contained in the alkali metal element layers is coordinated to the oxygen contained in the carboxylic acid anion to form a backbone. The alkali metal element may be one or more of Li, Na, and K, preferably Li. The alkali element contained in the alkali metal element layers is presumably not involved in ion migration during charge and discharge because it forms the backbone of the layered composition. As shown in FIG. 1, the layered composition thus constructed is formed by the organic backbone layers and the Li layers (alkali metal element layers) present between the organic backbone layers. In the energy storage mechanism of the layered composition, additionally, the organic backbone layers probably function as redox (e⁻) sites, whereas the Li layers probably function as Li⁺-absorbing sites. That is, the layered composition probably store and release energy as represented by formula (6). Furthermore, the organic backbone layers of the layered composition may have spaces into which Li can migrate, which presumably serve as sites capable of absorbing and releasing Li other than the alkali metal element layers in formula (6) to provide a higher charge-discharge capacity.

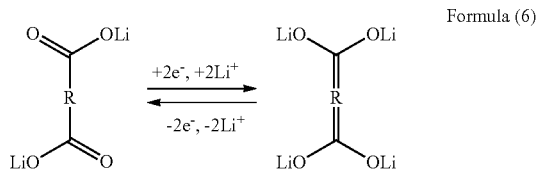

Formula (6)

The negative electrode of the nonaqueous secondary battery of the present invention may be formed by, for example, preparing a paste-like negative electrode mixture using a negative electrode active material made of the layered composition, a conductor, a binder, and a suitable solvent, applying the negative electrode mixture to a surface of a collector and drying it, and optionally compressing the coating for higher electrode density. The conductor may be any electron-conducting material that does not adversely affect the battery performance of the negative electrode, for example, one or a mixture of two or more of graphites such as natural graphite (flaky graphite and scaly graphite) and artificial graphite, acetylene black, carbon black, Ketjen black, carbon whisker, needle coke, carbon fiber, metals (e.g., copper, nickel, aluminum, silver, and gold), and the like. For higher electron conductivity and coatability, carbon black and acetylene black are preferred. Examples of binders, which function to bind active material particles with conductor particles, include polytetrafluoroethylene (PTFE), polyvinylidene fluoride (PVDF), fluorine-containing resins such as fluororubbers, thermoplastic resins such as polypropylene and polyethylene, ethylene-propylene-dienemer (EPDM), sulfonated EPDM, and natural butyl rubber (NBR), which can be used alone or as a mixture of two or more. Other examples include water-based binders such as cellulose binders and aqueous styrene-butadiene rubber (SBR) dispersions. Examples of solvents for dispersing the negative electrode active material, the conductor, and the binder include organic solvents such as N-methylpyrrolidone, dimethylformamide, dimethylacetoamide, methyl ethyl ketone, cyclohexanone, methyl acetate, methyl acrylate, diethyltriamine, N,N-dimethylaminopropylamine, ethylene oxide, and tetrahydrofuran. The active material can also be slurried with, for example, a latex of SBR in water containing a dispersant and a thickener. Examples of thickeners include polysaccharides such as carboxymethyl cellulose and methyl cellulose, which can be used alone or as a mixture of two or more. Examples of coating techniques include roller coating using applicator rollers, screen coating, doctor blade coating, spin coating, and bar coating, any of which can be used to provide any thickness and shape. Examples of collectors include copper, nickel, stainless steel, titanium, aluminum, baked carbon, conductive polymer, conductive glass, and Al—Cd alloy collectors, as well as collectors formed of copper or the like and surface-treated with carbon, nickel, titanium, silver, or the like for improved adhesion, conductivity, and reduction resistance. The collector of the negative electrode is preferably formed of aluminum metal. That is, the layered composition is preferably formed on an aluminum metal collector. This is because aluminum is abundant and is highly resistant to corrosion. Such collectors can also be surface-treated by oxidation. Examples of shapes of collectors include foils, films, sheets, nets, punched or expanded shapes, laths, porous shapes, foams, and fiber bundles. The collector has a thickness of, for example, 1 to 500 μm.

The positive electrode of the nonaqueous secondary battery of the present invention may be formed by, for example, preparing a paste-like positive electrode mixture using a positive electrode active material, a conductor, a binder, and a suitable solvent, applying the positive electrode mixture to a surface of a collector and drying it, and optionally compressing the coating for higher electrode density. Examples of positive electrode active materials include sulfides containing a transition metal element and oxides containing lithium and a transition metal element. Specific examples include transition metal sulfides such as $TiS_2$, $TiS_3$, $MoS_3$, and $FeS_2$; lithium manganese multiple oxides such as $Li_{(1-a)}MnO_2$ (e.g., 0<a<1, which applies hereinafter) and $Li_{(1-a)}Mn_2O_4$; lithium cobalt multiple oxides such as $Li_{(1-a)}CoO_2$; lithium nickel multiple oxides such as $Li_{(1-a)}NiO_2$; lithium vanadium multiple oxides such as $LiV_2O_3$; and transition metal oxides such as $V_2O_5$. Particularly preferred are transition metal multiple oxides of lithium, including $LiCoO_2$, $LiNiO_2$, $LiMnO_2$, and $LiV_2O_3$. Examples of conductors, binders, and solvents used for the positive electrode include those illustrated for the negative electrode. Examples of collectors for the positive electrode include aluminum, titanium, stainless steel, nickel, iron, baked carbon, conductive polymer, and conductive glass collectors, as well as collectors formed of aluminum, copper, or the like and surface-treated with carbon, nickel, titanium, silver, or the like for improved adhesion, conductivity, and oxidation resistance. Such collectors can also be surface-treated by oxidation. The shape of the collector may be similar to that of the collector for the negative electrode.

The ion-conducting medium of the nonaqueous secondary battery of the present invention may be, for example, a nonaqueous electrolyte solution or nonaqueous gel electrolyte solution containing a support salt. Examples of solvents for nonaqueous electrolyte solutions include carbonates, esters, ethers, nitriles, furans, sulfolanes, and dioxolanes, which can be used alone or as a mixture. Specific examples include, as carbonates, cyclic carbonates such as ethylene carbonate, propylene carbonate, vinylene carbonate, butylene carbonate, and chloroethylene carbonate and linear carbonates such as dimethyl carbonate, ethyl methyl carbonate, diethyl carbonate, ethyl-n-butyl carbonate, methyl-t-butyl carbonate, di-1-propyl carbonate, and t-butyl-i-propyl carbonate; cyclic esters such as γ-butyrolactone and γ-valerolactone; linear esters such as methyl formate, methyl acetate, ethyl acetate, and methyl lactate; ethers such as dimethoxyethane, ethoxymethoxyethane, and diethoxyethane; nitriles such as acetonitrile and benzonitrile; furans such as tetrahydrofuran and methyltetrahydrofuran; sulfolanes such as sulfolane and tetramethylsulfolane; and dioxolanes such as 1,3-dioxolane and methyldioxolane. Particularly preferred are combinations of a cyclic carbonate and a linear carbonate. Such combinations are advantageous not only in terms of cyclability, which indicates battery properties after repeated charge and discharge, but also in terms of the balance of the properties such as the viscosity of the electrolyte solution, the electrical capacity of the resulting battery, and the output of the battery. The cyclic carbonate probably increases the dielectric constant of the electrolyte solution because of its relatively high dielectric constant, whereas the linear carbonate probably reduces the viscosity of the electrolyte solution.

In addition, the ion-conducting medium of the present invention preferably contains a halogenated carbonate. In this case, during initial absorption of alkali metal ions into the layered composition, which serves as an electrode active material, the halogenated carbonate is reduced to form an alkali halide (e.g., lithium fluoride), which stabilizes the interface of the electrode active material. This improves the charge-discharge cyclability of the nonaqueous secondary battery. Examples of halogens include fluorine, chlorine, bromine, and iodine, of which fluorine is preferred for its high chemical stability. More preferably, the ion-conducting medium contains a cyclic halogenated carbonate and a linear halogenated carbonate. For example, the content of the cyclic halogenated carbonate is preferably 20% to 80% by volume, more preferably 40% to 60% by volume, of the total amount of cyclic and linear halogenated carbonates. If the content is 20% to 80% by volume, the charge-discharge cyclability can be improved. For example, the content of the linear halogenated carbonate is preferably 20% to 80% by volume, more preferably 40% to 60% by volume, of the total amount of cyclic and linear halogenated carbonates. If the content is 20% to 80% by volume, the charge-discharge cyclability can be improved. In addition, the contents of the cyclic and linear halogenated carbonates may be 50% by volume of the total amount of cyclic and linear halogenated carbonates. Examples of cyclic halogenated carbonates include carbonates, such as ethylene carbonate, propylene carbonate, and butylene carbonate, whose functional groups are partially halogenated. Specific examples include 1,2-difluoroethylene carbonate (DFEC), fluoroethylene carbonate (FEC), 4,5-difluoro-4,5-dimethyl-[1,3]-dioxolan-2-one, 4-(2,2,3,3-tetrafluoro-propoxymethyl)-[1,3]-dioxolan-2-one, 4-(2,3,3,3-tetrafluoro-2-trifluoromethyl-propyl)-[1,3]-dioxolan-2-one, trifluoropropylene carbonate, and chloroethylene carbonate, of which 1,2-difluoroethylene carbonate is preferred. This improves the charge-discharge cyclability. Examples of linear halogenated carbonates include carbonates, such as dimethyl carbonate, ethyl methyl carbonate, and diethyl carbonate, whose functional groups are partially halogenated. Specific examples include trifluoroethyl trifluoropropyl carbonate, 3-(1,1,2,2-tetrafluoroethoxy)-1,1,2,2-tetrafluoropropane ($CHF_2CF_2CH_2OCF_2CF_2H$), 3-(2-chloro-1,1,2-trifluoroethoxy)-1,1,2,2-tetrafluoropropane ($CHF_2CF_2CH_2OCF_2CFClH$), ethyl-2,2-difluoroacetate ($CHF_2COOCH_2CH_3$), 2,2,2-trifluoroethyl methyl carbonate ($CF_3CH_2OCOOCH_2CF_3$), bis-(2,2,2-trifluoroethyl)carbonate ($CF_3CH_2OCOOCH_2CF_3$), and bis-(2,2,3,3-tetrafluoropropyl)carbonate ($CHF_2CF_2CH_2OCOOCH_2CF_2CF_2H$), of which trifluoroethyl trifluoropropyl carbonate is preferred. Other examples include 2-trifluoromethyl-3-methoxyperfluoropentane ($CF_3CF(CF_3)CF(OCH_3)CF_2CF_3$) and 2-trifluoro-2-fluoro-3-difluoropropoxy-3-difluoro-4-fluoro-5-trifluoropentane ($CF_3CHFCF_2CH(CH_3)OCF_2CHFCF_3$).

If the layered composition contained as an electrode active material in the nonaqueous secondary battery electrode includes organic backbone layers having a fused polycyclic structure including two or more fused aromatic rings, the ion-conducting medium preferably contains a halogenated carbonate in an amount of 60% to 100% by volume, more preferably 70% by volume or more, further preferably 75% by volume or more, of the total amount of ion-conducting medium. If the content is 60% to 100% by volume, the charge-discharge cyclability can be further improved. As used herein, the term "organic backbone layers having a fused polycyclic structure" refers to organic backbone layers having a structure, such as naphthalene or anthracene, that includes two or more fused aromatic rings, for example, organic backbone layers having a structure such as 2,6-naphthaleledicarboxylic acid. In addition, if the layered composition contained as an electrode active material in the nonaqueous secondary battery electrode includes organic backbone layers having a fused polycyclic structure, the ion-conducting medium preferably contains at least one of a cyclic halogenated carbonate and a linear halogenated carbonate in an amount of 30% to 50% by volume of the total amount of nonaqueous electrolyte solution. If the content is 30% to 50% by volume, a higher cyclability is provided. An example of a cyclic halogenated carbonate is 1,2-difluoroethylene carbonate, whereas an example of linear halogenated carbonate is trifluoroethyl trifluoropropyl carbonate.

If the layered composition contained as an electrode active material in the nonaqueous secondary battery electrode includes organic backbone layers having a non-fused polycyclic structure including two or more linked aromatic rings, the ion-conducting medium preferably contains a halogenated carbonate in an amount of 40% to 100% by volume, more preferably 50% by volume or more, further preferably 60% by volume or more, of the total amount of ion-conducting medium. If the content is 40% to 100% by volume, the charge-discharge cyclability can be further improved. The term "organic backbone layers having a non-fused polycyclic structure" refers to organic backbone layers having a structure, such as biphenyl or triphenyl, that includes two or more linked aromatic rings, for example, organic backbone layers having a structure such as 4,4'-biphenyldicarboxylic acid. In addition, if the layered composition contained as an electrode active material in the nonaqueous secondary battery electrode includes organic backbone layers having a non-fused polycyclic structure, the ion-conducting medium preferably contains at least one of a cyclic halogenated carbonate and a linear halogenated carbonate in an amount of 20% to 50% by volume of the total amount of nonaqueous electrolyte solution. If the content is 20% to 50% by volume, the charge-discharge cyclability can be further improved. An example of a cyclic halogenated carbonate is 1,2-difluoroethylene carbonate, whereas an example of linear halogenated carbonate is trifluoroethyl trifluoropropyl carbonate.

Examples of support salts contained in the nonaqueous secondary battery of the present invention include $LiPF_6$, $LiBF_4$, $LiAsF_6$, $LiCF_3SO_3$, $LiN(CF_3SO_2)_2$, $LiC(CF_3SO_2)_3$, $LiSbF_6$, $LiSiF_6$, $LiAlF_4$, $LiSCN$, $LiClO_4$, $LiCl$, $LiF$, $LiBr$, $LiI$, and $LiAlCl_4$. In particular, one or a combination of two or more salts selected from the group consisting of inorganic salts such as $LiPF_6$, $LiBF_4$, $LiAsF_6$, and $LiClO_4$ and organic salts such as $LiCF_3SO_3$, $LiN(CF_3SO_2)_2$, and $LiC(CF_3SO_2)_3$ is preferably used for improved electrical properties. The concentration of the electrolyte salt in the nonaqueous electrolyte solution is preferably 0.1 to 5 mol/L, more preferably 0.5 to 2 mol/L. An electrolyte salt concentration of 0.1 mol/L or more provides sufficient current density, whereas an electrolyte salt concentration of 5 mol/L or less improves the stability of the electrolyte solution. The nonaqueous electrolyte solution may contain a flame retardant such as a phosphorus- or halogen-containing flame retardant.

Instead of a liquid ion-conducting medium, the ion-conducting medium may be a solid ion-conducting polymer. The ion-conducting polymer may be a polymer gel containing a polymer, such as acrylonitrile, ethylene oxide, propylene oxide, methyl methacrylate, vinyl acetate, vinylpyrrolidone, or polyvinylidene fluoride, and a support salt. The ion-conducting polymer may also be used in combination with a nonaqueous electrolyte solution. In addition to ion-conducting polymers, examples of available ion-conducting media include inorganic solid electrolytes, mixtures of organic polymer electrolytes and inorganic solid electrolytes, and inorganic solid powders bound by organic binders.

The nonaqueous secondary battery of the present invention may include a separator between the positive electrode and the negative electrode. The separator may be formed of any composition that can be used in the operating range of the nonaqueous secondary battery, including polymer nonwoven fabrics such as polypropylene and polyphenylene sulfide nonwoven fabrics and thin microporous films of olefin resins such as polyethylene and polypropylene. They may be used alone or as a mixture thereof.

Figure 2:
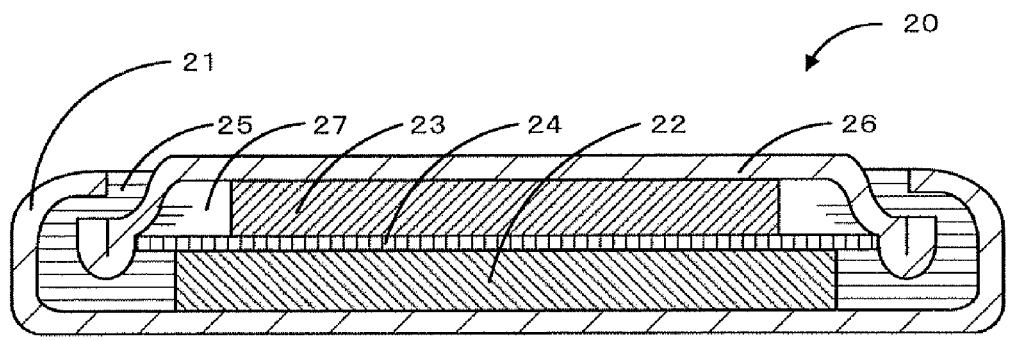
FIG. 2 is a schematic view showing an example of a nonaqueous secondary battery 20 of the present invention.

Examples of shapes of the nonaqueous secondary battery of the present invention include, but not limited to, coins, buttons, sheets, laminates, cylinders, flat shapes, and rectangles. The nonaqueous secondary battery is also applicable to large batteries for use with, for example, electric cars. FIG. 2 is a schematic view showing an example of a nonaqueous secondary battery 20 of the present invention. This nonaqueous secondary battery 20 includes a cup-shaped battery case 21, a positive electrode 22 containing a positive electrode active material and disposed on the bottom of the battery case 21, a negative electrode 23 containing a negative electrode active material and disposed opposite the positive electrode 22 with a separator 24 therebetween, a gasket 25 formed of an insulator, and a sealing plate 26 disposed at the opening of the battery case 21 to seal the battery case 21 with the gasket 25 therebetween. A space between the positive electrode 22 and the negative electrode 23 in the nonaqueous secondary battery 20 is filled with an ion-conducting medium 27 containing an alkali metal salt (lithium salt). The negative electrode 23 contains, as a negative electrode active material, a layered composition including organic backbone layers containing an aromatic compound that is a dicarboxylic acid anion having two or more aromatic ring structures and having the two carboxylic acid anions of the dicarboxylic acid anion bonded to diagonally opposite positions of the aromatic compound and alkali metal element layers having an alkali metal element coordinated to oxygen contained in the carboxylic acid anion.

In the nonaqueous secondary battery of the present invention, the layered composition, serving as an active material, has four coordination bonds between Li and the oxygen in the dicarboxylic acid, which presumably makes it insoluble in the nonaqueous electrolyte solution to maintain its crystal structure, thus improving the stability of the charge-discharge cyclability. In the layered composition, the organic backbone layers presumably function as redox sites, whereas the Li layers presumably function as Li-ion absorbing sites. In addition, the negative electrode has a charge-discharge potential of 0.5 to 1.0 V with respect to lithium metal, which prevents a significant decrease in energy density due to a decrease in the operating voltage of the battery and also prevents precipitation of lithium metal. This novel layered composition (crystalline organic-inorganic composite material) presumably improves the charge-discharge properties.

It should be understood that the present invention is not limited to the above embodiment but can be practiced in various embodiments within the technical scope of the present invention.

For example, although the above embodiment illustrates a nonaqueous secondary battery, a nonaqueous secondary battery electrode may also be provided.

Although the above embodiment illustrates, by way of example, a positive electrode including a collector having a positive electrode mixture, which contains a positive electrode active material, provided thereon and a negative electrode including a collector having a negative electrode mixture, which contains a negative electrode active material, provided thereon, a bipolar electrode may also be provided that includes a collector having a positive electrode mixture, which contains a positive electrode active material, provided on one side thereof and a negative electrode mixture, which contains a negative electrode active material, provided on the other side thereof. That is, the nonaqueous secondary battery electrode of the present invention may include a positive electrode mixture containing a positive electrode active material that absorbs and releases an alkali metal, a negative electrode mixture containing the layered composition described above as a negative electrode active material that absorbs and releases the alkali metal, and a collector having the positive electrode mixture provided on one side thereof and the negative electrode mixture provided on the other side thereof and formed of a collector metal that dissolves at a potential lower than the redox potential of the positive electrode active material and that undergoes an alloying reaction with the alkali metal at a potential higher than the redox potential of the negative electrode active material. This eliminates the need to use collectors of different materials for the positive and negative electrodes, which reduces the complexity involved in the manufacturing process, including material procurement and separate formation of the positive and negative electrodes, and also reduces the volume of the collector in the secondary battery. In addition, a plurality of nonaqueous secondary batteries can be efficiently connected by stacking a plurality of bipolar electrodes with an ion-conducting medium therebetween.

The alkali metal that is absorbed into and released from the bipolar electrode during charge and discharge may be the same as or different from the alkali metal element in the alkali metal element layers of the layered composition, for example, one or more of Li, Na, K, and the like, of which Li is preferred for higher energy density. For illustration purposes, a bipolar electrode that uses Li as the alkali metal that is absorbed and released during charge and discharge will be described below by way of example. The collector metal used for the bipolar electrode is preferably aluminum metal. The alloying reaction between aluminum and lithium occurs at 0.27 V with respect to lithium metal. The layered composition of the present invention undergoes a charge-discharge reaction mainly in the range of 0.7 to 0.85 V with respect to lithium metal. Thus, aluminum metal can be used as a collector metal that dissolves at a potential lower than the redox potential of the positive electrode active material and that undergoes an alloying reaction with the alkali metal at a potential higher than the redox potential of the negative electrode active material.

The positive electrode mixture of the bipolar electrode may contain a positive electrode active material that is operable with a negative electrode containing the negative electrode active material of the present invention for nonaqueous secondary batteries. For example, the positive electrode active material contained in the positive electrode mixture may be at least one of a positive electrode active material having a spinel structure represented by the general formula $LiNi_xMn_{2-x}O_4$ (where $0 \le x \le 0.5$) and a positive electrode active material having a layered structure represented by the general formula $LiNi_{1-y}M_yO_2$ (where $0 \le y \le 0.5$, preferably $y \le 0.2$, and M is one or more selected from Mg, Ti, Cr, Fe, Co, Cu, Zn, Al, Ge, and Sn). Specific examples include materials having a spinel structure such as $LiMn_2O_4$ and $LiNi_{0.5}Mn_{1.5}O_4$ and materials having a layered rock salt structure such as $LiCoO_2$, $LiNiO_2$, $LiNi_{0.5}Mn_{0.5}O_2$, and $LiNi_{0.8}Co_{0.15}Al_{0.05}O_2$. Particularly preferred are materials having a spinel structure, which provide a higher battery voltage. In the bipolar electrode, the average charge-discharge potential difference between the positive electrode side where the positive electrode mixture is provided and the negative electrode side where the negative electrode mixture is provided is preferably 3.0 V or more, more preferably 4.0 V or more. For example, the use of the layered composition as a negative electrode active material in combination with a positive electrode active material having the layered structure as shown above provides an average charge-discharge potential difference of 3.0 V or more. In addition, the use of the layered composition as a negative electrode active material in combination with a positive electrode active material having the spinel structure as shown above provides an average charge-discharge potential difference of 4.0 V or more.

Figure 3:
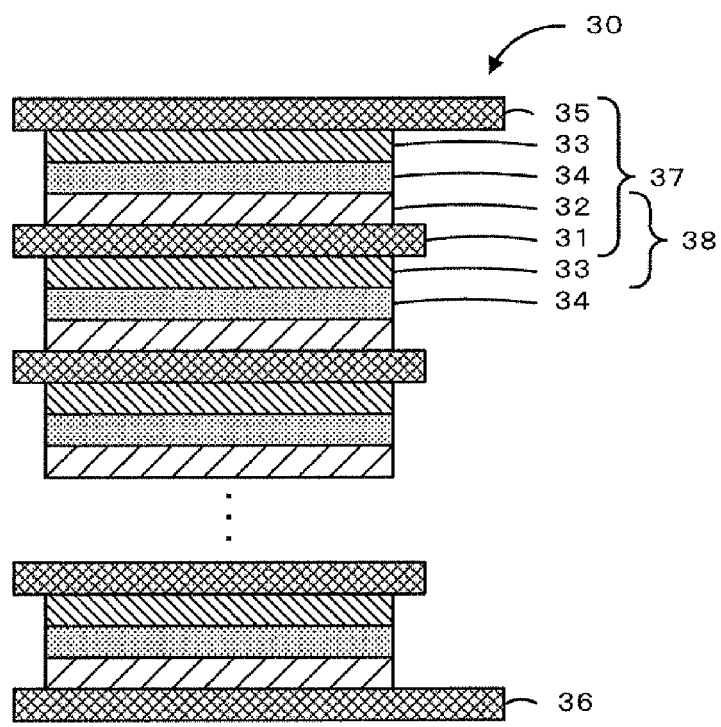
FIG. 3 is a schematic view showing an example of an assembled battery 30 of the present invention.
Figure 4:
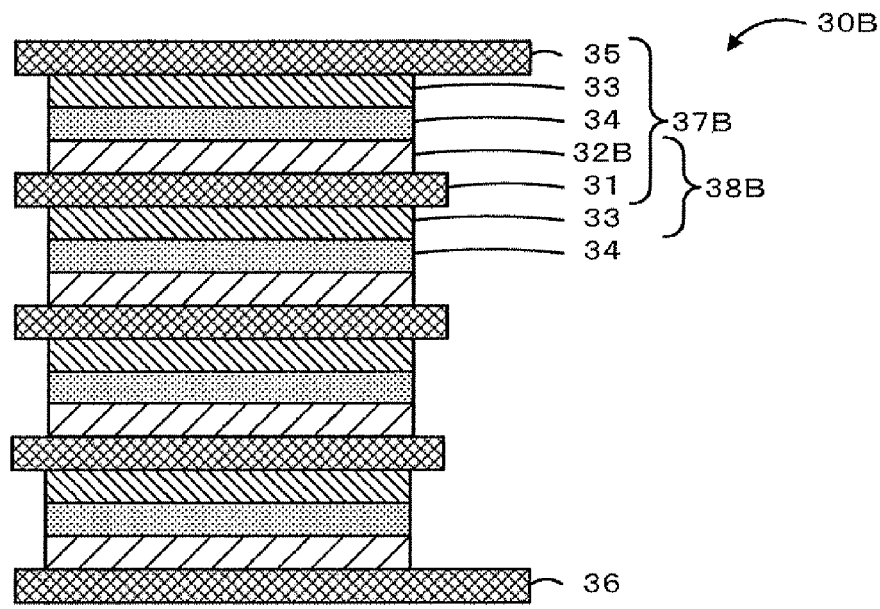
FIG. 4 is a schematic view showing an example of an assembled battery 30B of the present invention.
Figure 5:
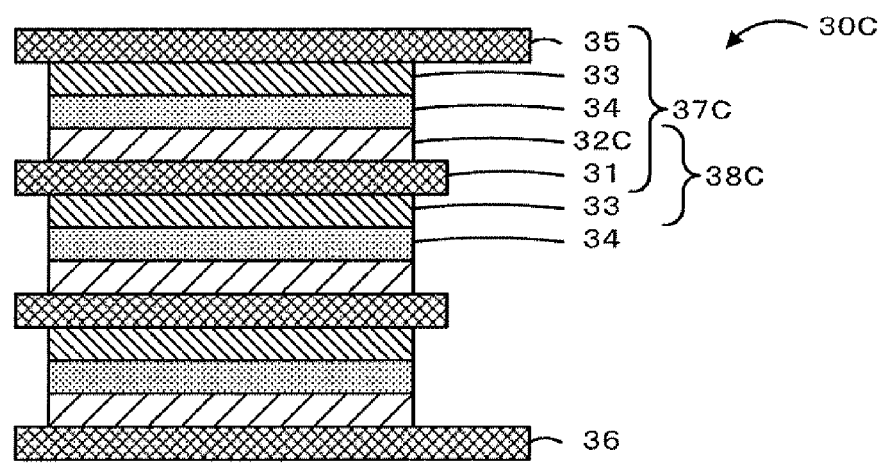
FIG. 5 is a schematic view showing an example of an assembled battery 30C of the present invention.

Although the above embodiment illustrates a nonaqueous secondary battery including a positive electrode, a negative electrode, and an ion-conducting medium (see FIG. 2), an assembled battery may also be provided that includes a plurality of connected nonaqueous secondary batteries, each including the above bipolar nonaqueous secondary battery electrode and an ion-conducting medium that conducts alkali metal ions. FIG. 3 is a schematic view showing an example of an assembled battery 30 of the present invention. In addition, FIG. 4 is a schematic view showing an example of an assembled battery 30B of the present invention. In addition, FIG. 5 is a schematic view showing an example of an assembled battery 30C of the present invention. As shown in FIG. 3, the assembled battery 30 includes a negative electrode collector terminal 35 disposed at one end thereof, a positive electrode collector terminal 36 disposed at the other end thereof, and a plurality of bipolar electrodes 38 stacked on top of each other with an ion-conducting medium 34 therebetween. Each bipolar electrode 38 includes a collector 31, a positive electrode mixture layer 32, and a negative electrode mixture layer 33, and the collector 31 has the positive electrode mixture layer 32 disposed on one side thereof and the negative electrode mixture layer 33 disposed on the other side thereof. The positive electrode mixture layer 32, the ion-conducting medium 34, and the negative electrode mixture layer 33 are disposed in that order between the collectors 31 of the adjacent bipolar electrodes 38 to form a battery cell 37. Thus, the assembled battery 30 includes a plurality of stacked battery cells 37 sharing the collectors 31. The use of the bipolar electrodes 38 in this manner allows a plurality of battery cells 37 to be more efficiently stacked on top of each other.

The ion-conducting medium 34 of the assembled battery of the present invention may be a liquid medium, although solid and solid-like media are preferred, including polymer gel electrolytes and all-solid electrolytes. This facilitates stacking of the bipolar electrodes 38 and the ion-conducting medium 34. Examples of all-solid electrolytes include inorganic compounds such as the garnet-type oxide $Li_7La_3Zr_2O_{12}$, the glass ceramic $Li_{1.5}Al_{0.5}Ge_{1.5}(PO_4)_3$, and the glass ceramic $Li_{1+b}Ti_2Si_bP_{3-b}O_{12} \cdot AlPO_4$. A preferred example of a garnet-type oxide is one represented by the general formula $Li_{5+z}La_3(Zr_z,A_{2-z})O_{12}$ (where $1.4 \leq z < 2$ and A is one or more elements selected from the group consisting of Sc, Ti, V, Y, Nb, Hf, Ta, Al, Si, Ga, and Ge). This is because it has a wide potential window and a higher lithium conductivity. In addition, as described above, the collectors 31 of the assembled battery of the present invention are preferably formed of aluminum. In addition, the alkali metal that is absorbed and released during charge and discharge is preferably lithium.

For example, if the assembled battery of the present invention uses bipolar electrodes 38B including a positive electrode mixture layer 32B containing a positive electrode active material having a layered structure represented by the general formula $LiNi_{1-y}M_yO_2$ (where $0 \leq y \leq 0.5$ and M is one or more selected from Mg, Ti, Cr, Fe, Co, Cu, Zn, Al, Ge, and Sn), as shown in FIG. 4, an assembled battery 30B including four stacked battery cells 37B can be provided as a 12 V grade stacked assembled battery. In addition, for example, if the assembled battery of the present invention uses bipolar electrodes 38C including a positive electrode mixture layer 32C containing a positive electrode active material having a spinel structure represented by the general formula $LiNi_xMn_{2-x}O_4$ (where $0 \leq x \leq 0.5$), an assembled battery 30C including three stacked battery cells 37C can be provided as a 12 V grade stacked assembled battery. Thus, an assembled battery having the desired battery voltage can be easily designed by changing the desired positive electrode active material and the number of stacked battery cells.

In the bipolar electrode (nonaqueous secondary battery electrode) and the assembled battery including bipolar electrodes described in detail above, the positive electrode mixture and the negative electrode mixture can be provided on either side of the collector because little alloying reaction occurs between the collector metal and the alkali metal. This allows efficient connection of a plurality of nonaqueous secondary batteries including an ion-conducting medium that conducts alkali metal ions and a bipolar electrode including a collector metal that dissolves at a potential lower than the redox potential of the positive electrode active material and that undergoes an alloying reaction with the alkali metal at a potential higher than the redox potential of the negative electrode active material. Thus, an assembled battery (nonaqueous secondary battery) having high energy density can be more easily provided.

EXAMPLES

Specific examples of fabrication of nonaqueous secondary batteries of the present invention will be described below as the Examples.

Example 1

Lithium 2,6-naphthaleledicarboxylate (see formula (7)) was synthesized as a layered composition. The starting materials used for synthesis of lithium 2,6-naphthaleledicarboxylate were 2,6-naphthaleledicarboxylic acid and lithium hydroxide monohydrate ($LiOH \cdot H_2O$). First, 100 mL of methanol was added to 0.556 g of lithium hydroxide monohydrate, and it was stirred. After the lithium hydroxide monohydrate was dissolved, 1.0 g of 2,6-naphthaleledicarboxylic acid was added, and it was stirred for one hour. After stirring, the solvent was removed, and the residue was dried in vacuo at 150° C. for 16 hours to yield a white powder sample. The resulting white powder sample is referred to as an active material powder of Example 1.

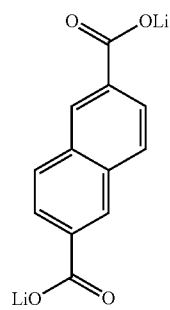

Formula (7)

Fabrication of Coated Electrode

A nonaqueous secondary battery electrode was fabricated using the active material powder of Example 1. A slurried mixture was prepared by mixing 60% by mass of the lithium 2,6-naphthaleledicarboxylate of Example 1, 30% by mass of carbon black as a conductor, and 10% by mass of polyvinylidene fluoride as a binder and dispersing the mixture using an appropriate amount of N-methyl-2-pyrrolidone as a dispersant. The slurried mixture was uniformly applied to a 10 μm thick copper foil collector and was dried by heating to fabricate a coated sheet. The coated sheet was then pressed and punched to prepare a circular electrode having an area of 2.05 cm².

Fabrication of Bipolar Test Cell

A nonaqueous electrolyte solution was prepared by adding lithium hexafluorophosphate to a concentration of 1 mol/L in a nonaqueous solvent containing ethylene carbonate, dimethyl carbonate, and ethyl methyl carbonate in a volume ratio of 30:40:30. A bipolar test cell was fabricated by holding a separator (Tonen Tapyrus Co., Ltd.) impregnated with the above nonaqueous electrolyte solution between the above electrode, serving as a working electrode, and a lithium metal foil (300 μm thick), serving as a counter electrode. The resulting cell is referred to as a bipolar test cell of Example 1.

Example 2

A white powder sample was yielded as an active material powder of Example 2 by repeating the procedure of Example 1 except that the lithium 2,6-naphthaleledicarboxylate of Example 1 was replaced by lithium 4,4'-biphenyldicarboxylate (see formula (8)). Also, a nonaqueous secondary battery electrode of Example 2 was fabricated by repeating the procedure of Example 1 using the active material powder of Example 2, and a bipolar test cell was fabricated using the nonaqueous secondary battery electrode of Example 2.

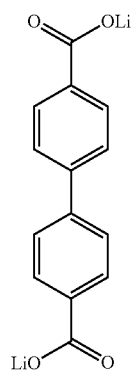

Formula (8)

Comparative Example 1

A white powder sample was yielded as an active material powder of Comparative Example 1 by repeating the procedure of Example 1 except that the lithium 2,6-naphthaleledicarboxylate of Example 1 was replaced by lithium terephthalate (see formula (9)). Also, a nonaqueous secondary battery electrode of Comparative Example 1 was fabricated by repeating the procedure of Example 1 using the active material powder of Comparative Example 1, and a bipolar test cell was fabricated using the nonaqueous secondary battery electrode of Comparative Example 1.

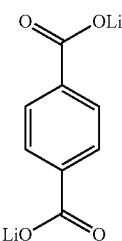

Formula (9)

Comparative Example 2

A white powder sample was yielded as an active material powder of Comparative Example 2 by repeating the procedure of Example 1 except that the lithium 2,6-naphthaleledicarboxylate of Example 1 was replaced by lithium 2,3-naphthaleledicarboxylate (see formula (10)). Also, a nonaqueous secondary battery electrode of Comparative Example 2 was fabricated by repeating the procedure of Example 1 using the active material powder of Example 2, and a bipolar test cell was fabricated using the nonaqueous secondary battery electrode of Comparative Example 2.

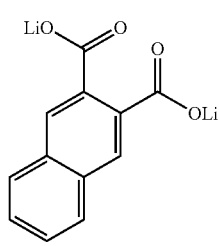

Formula (10)

X-Ray Diffraction Measurement

Figure 6:
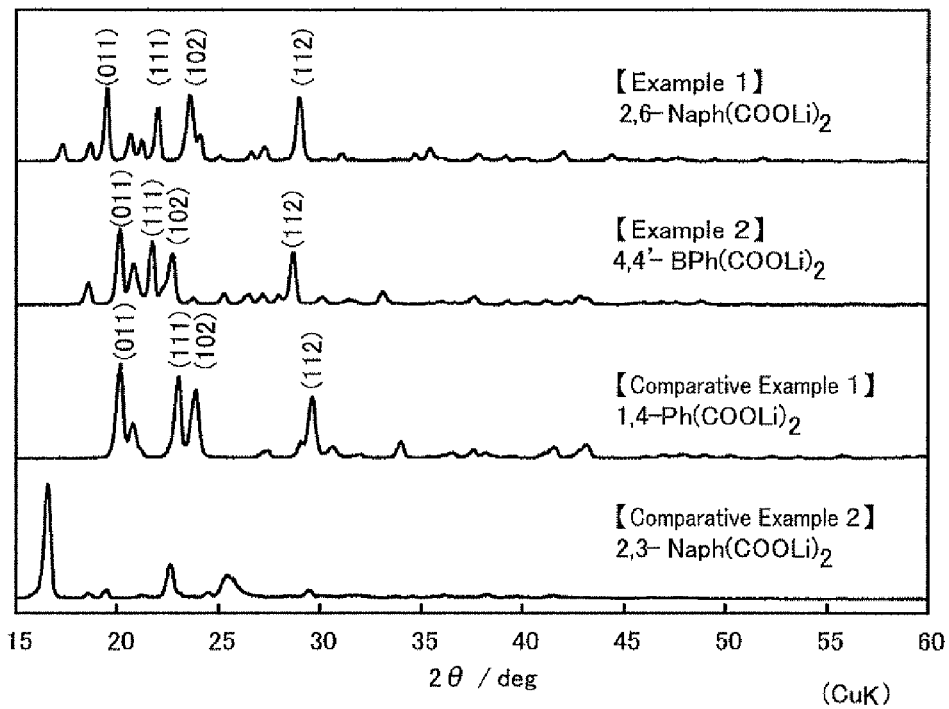
FIG. 6 shows the results of X-ray diffraction measurement for Examples 1 and 2 and Comparative Examples 1 and 2.

Powdered X-ray diffraction measurement was performed on the active material powders of Examples 1 and 2 and Comparative Examples 1 and 2. In the measurement, the Cu—Kα line (wavelength: 1.54051 Å) was used as radiation, and an X-ray diffractometer (Rigaku RINT-2200) was used. In the measurement, additionally, a single-crystal graphite monochromator was used as a monochromatic X-ray source, the applied voltage was set to 40 kV, the current was set to 30 mA, the scan rate was set to 4°/min, and the angular range was set to 2θ=10° to 90°. FIG. 6 shows the results of the X-ray diffraction measurement for Examples 1 and 2 and Comparative Examples 1 and 2. As shown in FIG. 6, the active material powders of Examples 1 and 2 and Comparative Example 1 presumably had a layered structure of lithium layers and organic backbone layers as shown in FIG. 1 because they showed clear (001), (111), (102), and (112) peaks based on the assumption that they were monoclinic crystals belonging to the space group $P2_1/c$. In addition, because the active material powders of Examples 1 and 2 and Comparative Example 1 were monoclinic crystals belonging to the space group $P2_1/c$, they presumably had a structure in which the oxygen in four different aromatic dicarboxylic acid molecules formed four coordination bonds with lithium and had interaction between π-electron conjugated clouds in the organic backbone thereof. In contrast, the active material powder of Comparative Example 1, which is structurally unlikely to form alkali metal layers in view of the bond positions of the dicarboxylic acid anion, showed no peak attributed to the space group P2$_1$/c, demonstrating that it had a different crystal structure.

Simultaneous Thermogravimetry and Differential Calorimetry

Figure 7:
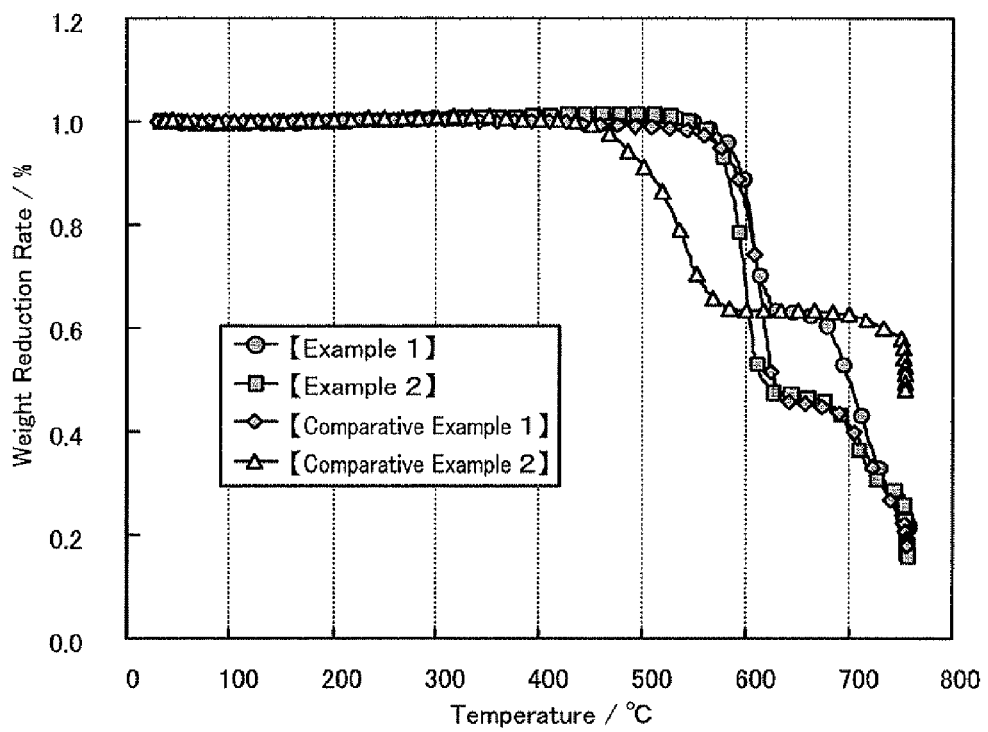
FIG. 7 shows the results of simultaneous thermogravimetry and differential calorimetry for Examples 1 and 2 and Comparative Examples 1 and 2.

Simultaneous thermogravimetry and differential calorimetry was performed on the active material powders of Examples 1 and 2 and Comparative Examples 1 and 2. In the measurement, a simultaneous thermogravimeter-differential calorimeter (Rigaku Thermo Mass) was used. In the measurement, the measurement temperature range was set to room temperature to 750° C., and the heating rate was set to 10° C./rain. FIG. 7 shows the results of the simultaneous thermogravimetry and differential calorimetry for Examples 1 and 2 and Comparative Examples 1 and 2. Whereas the mass of the material of Comparative Example 1 started decreasing around 450° C., the masses of the materials of Examples 1 and 2 and Comparative Example 1 started decreasing around 550° C., demonstrating that they had improved thermal stability. This is presumably because the monoclinic crystal structures belonging to the space group P2$_1$/c in Examples 1 and 2 and Comparative Example 1 were organized by π-electron interaction and had four coordination bonds between oxygen from four different aromatic dicarboxylic acid molecules and lithium, thus forming a crystal with superior thermal stability.

Charge-Discharge Test

Figure 8:
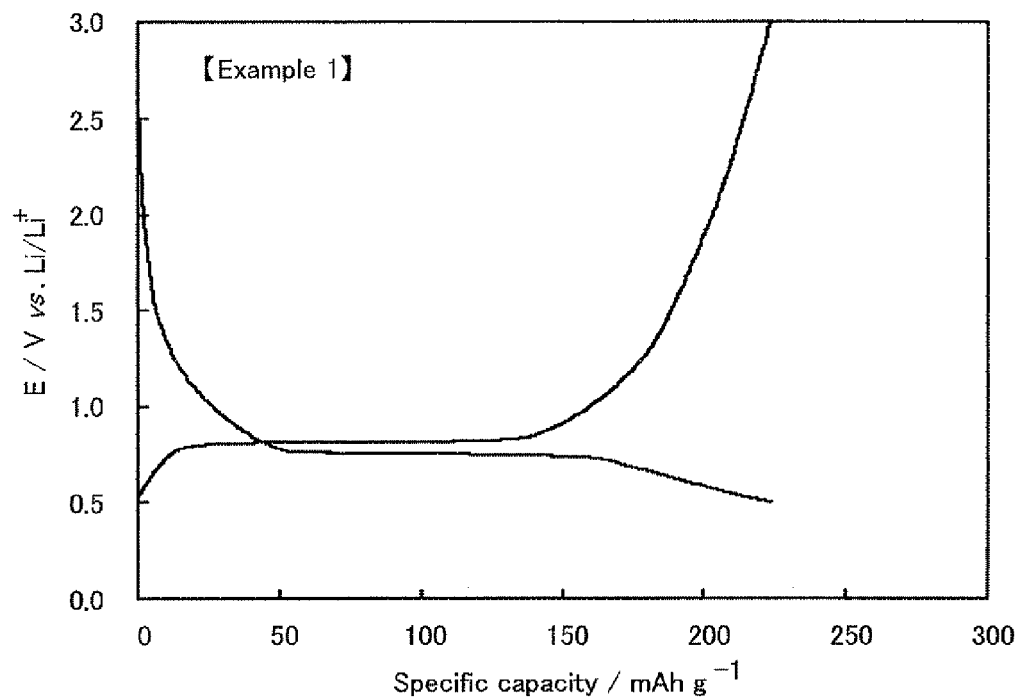
FIG. 8 shows a charge-discharge curve for Example 1.
Figure 9:
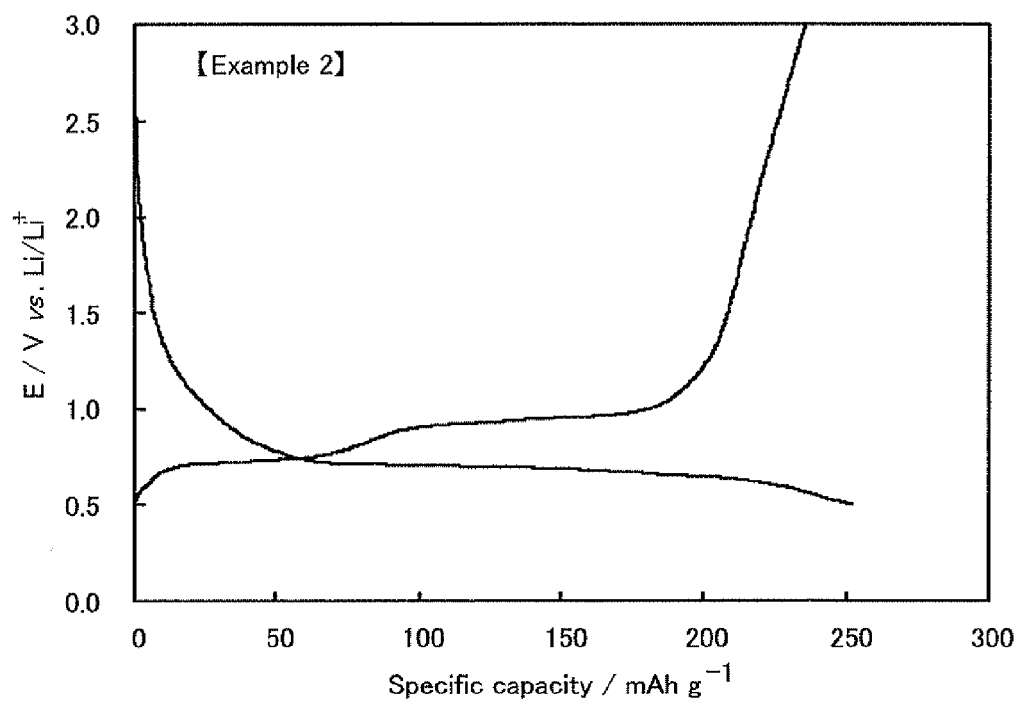
FIG. 9 shows a charge-discharge curve for Example 2.
Figure 10:
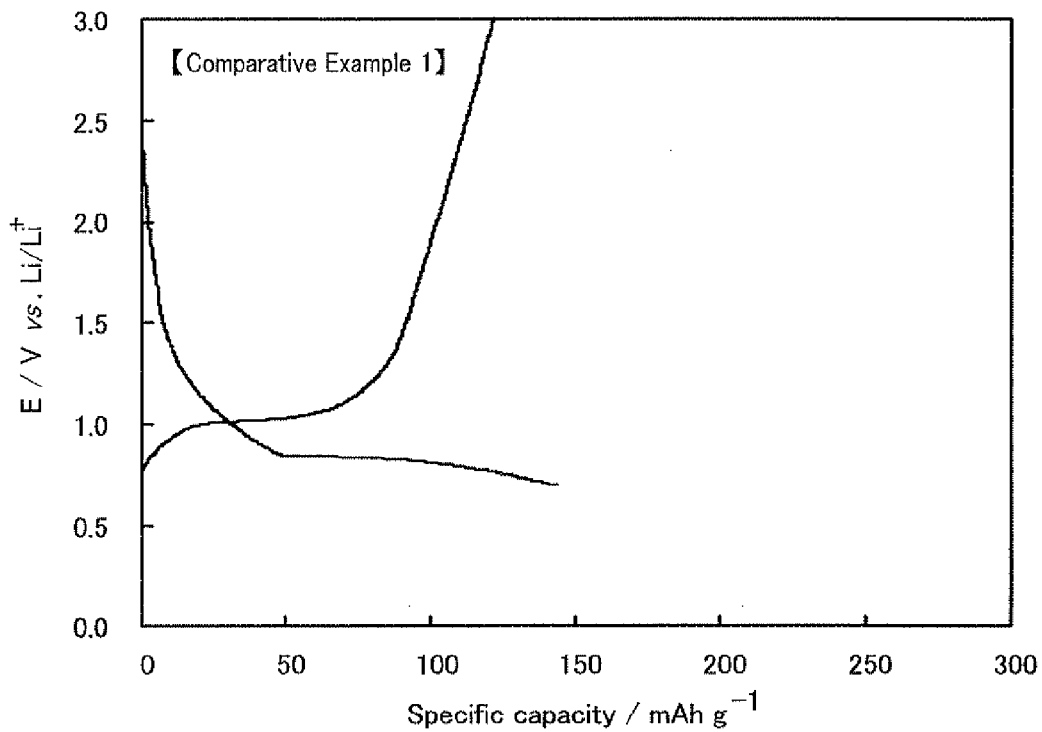
FIG. 10 shows a charge-discharge curve for Comparative Example 1.
Figure 11:
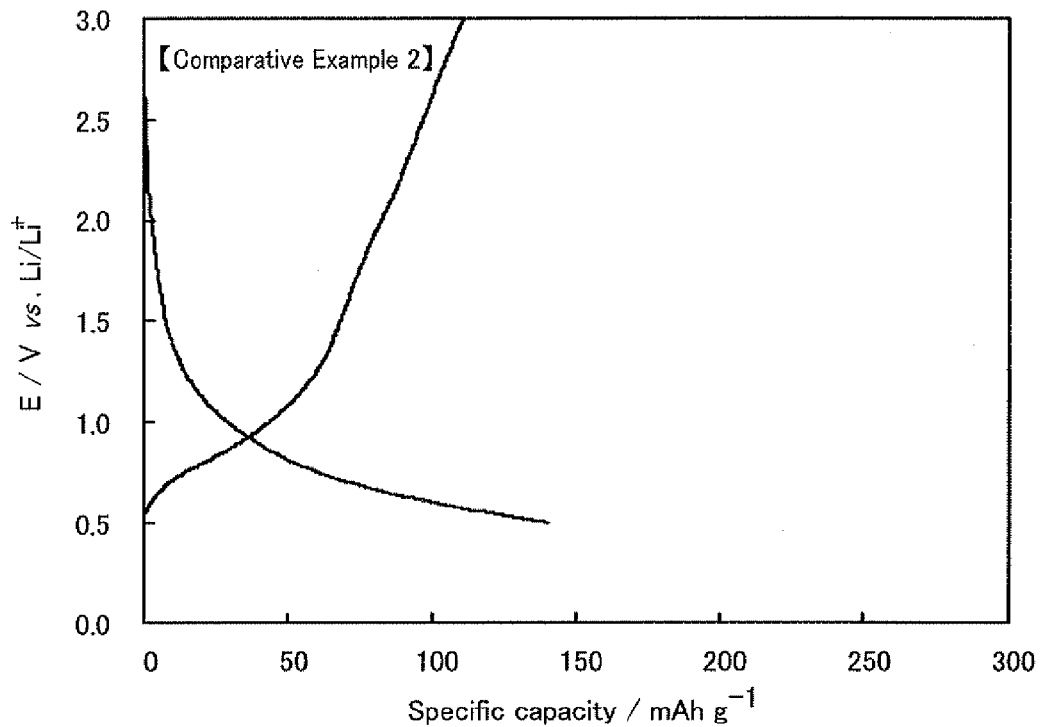
FIG. 11 shows a charge-discharge curve for Comparative Example 2.

In an environment with a temperature of 20° C., the bipolar test cells of Examples 1 and 2 and Comparative Examples 1 and 2 were reduced (charged) to 0.5 V at 0.02 mA and were then oxidized (discharged) to 3.0 V at 0.02 mA. The reduction capacity for the first charge-discharge operation was Q(1st)$_{red}$, and the oxidation capacity for the first charge-discharge operation was Q(1st)$_{oxi}$. FIG. 8 shows a charge-discharge curve for Example 1, FIG. 9 shows a charge-discharge curve for Example 2, FIG. 10 shows a charge-discharge curve for Comparative Example 1, and FIG. 11 shows a charge-discharge curve for Comparative Example 2. In addition, Table 1 summarizes the results of the charge-discharge test for the bipolar test cells of Examples 1 and 2 and Comparative Examples 1 and 2. As shown in FIGS. 8 to 11 and Table 1, the cells of Examples 1 and 2 of the present invention exhibited higher oxidation capacities than those of Comparative Example 1. For example, the cell of Example 2 exhibited an oxidation capacity higher than the theoretical capacity, i.e., 200 mAh/g. This is presumably because lithium was also absorbed into and released from the space formed in the organic backbone layers. In addition, whereas the cells of Examples 1 and 2 exhibited flat potential regions, i.e., plateau regions, the cell of Comparative Example 2 exhibited no clear plateau region. Presumably, therefore, with a layered structure of lithium layers and organic backbone layers, the cells of Examples 1 and 2 provide a flat potential region in the range of 0.7 to 0.85 V with respect to lithium metal. The cell of Comparative Example 1 had a lower charge-discharge capacity than Examples 1 and 2. This is presumably due to, for example, low conductivity because of the presence of only one aromatic ring. If there is only one aromatic ring, the π-electron interaction in the aromatic ring probably decreases with slight volume changes during absorption of lithium, which reduces the overlap of π-electrons and therefore decreases the conductivity, thus decreasing the charge-discharge capacity. In contrast, if there are two or more aromatic rings, the charge-discharge capacity probably does not decrease because their large overlap of π-electrons provides stable conductivity irrespective of volume changes during absorption of lithium. The number of aromatic rings is preferably about 2 to 5 because a large number of aromatic rings results in large organic backbone layers as compared with the lithium-absorbing sites. In addition, the cells of Examples 1 and 2 allow a high-voltage battery design because the plateau regions of Examples 1 and 2 are lower than that of Comparative Example 1. The potentials of the plateau regions with respect to lithium metal in Examples 1 and 2 were in the range of 0.7 to 0.85 V, which were higher than, for example, the potential of graphite as a negative electrode active material with respect to lithium metal, thus causing little lithium metal to precipitate on the negative electrode. In addition, the potentials with respect to lithium metal in Examples 1 and 2 were lower than the potential of a multiple oxide (e.g., lithium titanium oxide) as a negative electrode active material, i.e., 1.5 V, with respect to lithium metal, thus providing a higher battery voltage. In addition, the negative electrode active materials of Examples 1 and 2 were structurally and thermally more stable than metal silicon as a negative electrode active material, thus providing a higher charge-discharge cyclability. These results demonstrate that the layered compositions of the present invention (crystalline organic-inorganic composite materials) can be used as electrode active materials with superior charge-discharge cyclability.

TABLE 1

| Compound | Oxidation Capacity[1] Q(1st)$_{oxi}$ mAh/g | Plateau Potential[2] V vs. Li/Li$^+$ |
|---|---|---|
| Example 1 | Lithium 2,6-naphthaleledicarboxylate | 223 | 0.75 |
| Example 2 | Lithium 4,4'-biphenyldicarboxylate | 227 | 0.70 |
| Comparative Example 1 | Lithium terephthalate | 121 | 0.84 |
| Comparative Example 2 | Lithium 2,3-naphthaleledicarboxylate | 140 | — |

[1]Q(1st)$_{oxi}$: the oxidation capacity for the first charge-discharge operation
[2]Plateau potential: flat potential when charging in charge-discharge operation Next, research was conducted on bipolar electrodes of the present invention. Negative electrodes including an aluminum separator and a negative electrode active material layer formed thereon and positive electrodes including an aluminum separator and a positive electrode active material layer formed thereon were separately fabricated, and bipolar cells were assembled using the negative and positive electrodes to examine the charge-discharge properties thereof.

Example 3

A nonaqueous secondary battery electrode was fabricated using the active material powder of Example 1. A slurried mixture was prepared by mixing 60% by mass of the lithium 2,6-naphthaleledicarboxylate of Example 1, 10% by mass of vapor-grown carbon fiber (VGCF) as a conductor, 20% by mass of carbon black (conductive particles) as a conductor, and 10% by mass of polyvinylidene fluoride as a binder and dispersing the mixture using an appropriate amount of N-methyl-2-pyrrolidone as a dispersant. The BET specific surface area of the VGCF determined by nitrogen absorption was 13 m$^2$/g, and the average fiber length determined by measuring the length of fibers contained in an SEM image was 15 Rm. In addition, the BET specific surface area of the carbon black determined by nitrogen absorption was 225 m$^2$/g, and the average particle size determined by measuring the size of particles contained in an SEM image was 25 nm. The slurried mixture was uniformly applied to a 10 ml thick aluminum collector and was dried by heating to fabricate a coated sheet. The coated sheet was then pressed and punched to prepare a circular negative electrode having an area of 2.05 cm$^2$.

A positive electrode of Example 3 was fabricated as follows. A slurried mixture was prepared by mixing 85% by mass of LiNi$_{0.5}$Mn$_{1.5}$O$_4$ as a positive electrode active material, 10% by mass of carbon black as a conductor, and 5% by mass of polyvinylidene fluoride as a binder and dispersing the mixture using an appropriate amount of N-methyl-2-pyrrolidone as a dispersant. The slurried mixture was uniformly applied to a 10 μm thick aluminum collector and was dried by heating to fabricate a coated sheet. The coated sheet was then pressed and punched to prepare a circular positive electrode having an area of 2.05 cm$^2$.

Fabrication of Bipolar Test Cell

A nonaqueous electrolyte solution was prepared by adding lithium hexafluorophosphate to a concentration of 1 mol/L in a nonaqueous solvent containing ethylene carbonate, dimethyl carbonate, and ethyl methyl carbonate in a volume ratio of 30:40:30. A bipolar test cell was fabricated by holding a separator (Tonen Tapyrus Co., Ltd.) impregnated with the above nonaqueous electrolyte solution between the above positive and negative electrodes. The resulting cell is referred to as a bipolar test cell of Example 3.

Example 4

A bipolar test cell was fabricated as a bipolar test cell of Example 4 by repeating the procedure of Example 3 except that LiNi$_{0.8}$Co$_{0.15}$Al$_{0.05}$O$_2$ was used as a positive electrode active material.

Example 5

A bipolar test cell was fabricated as a bipolar test cell of Example 5 by holding a separator impregnated with the above nonaqueous electrolyte solution between the negative electrode of Example 3, serving as a working electrode, and a lithium metal foil (300 μm thick), serving as a counter electrode.

Comparative Example 3

A slurried mixture was prepared by mixing 95% by mass of a mixture of graphite and graphitizable carbon as a negative electrode active material and 5% by mass of polyvinylidene fluoride as a binder and dispersing the mixture using an appropriate amount of N-methyl-2-pyrrolidone as a dispersant. The negative electrode active material was a mixture of 60% by mass of graphite and 40% by mass of graphitizable carbon, where d$_{002}$=0.388 nm or less for graphite and d$_{002}$=0.34 nm or more for graphitizable carbon. The slurried mixture was uniformly applied to a 10 μm thick aluminum collector and was dried by heating to fabricate a coated sheet. The coated sheet was then pressed and punched to prepare a circular negative electrode having an area of 2.05 cm$^2$. A bipolar test cell was fabricated as a bipolar test cell of Comparative Example 3 by repeating the procedure of Example 3 except that the above negative electrode was used.

Comparative Example 4

A bipolar test cell was fabricated as a bipolar test cell of Comparative Example 4 by repeating the procedure of Example 3 except that the negative electrode of Comparative Example 3 and the positive electrode of Example 4 were used.

Comparative Example 5

A bipolar test cell was fabricated as a bipolar test cell of Comparative Example 5 by repeating the procedure of Example 3 except that lithium titanate (Li$_4$Ti$_5$O$_{12}$) was used as a negative electrode active material.

Comparative Example 6

A bipolar test cell was fabricated as a bipolar test cell of Comparative Example 6 by repeating the procedure of Example 3 except that the negative electrode of Comparative Example 5 and the positive electrode of Example 4 were used.

Comparative Example 7

A bipolar test cell was fabricated as a bipolar test cell of Comparative Example 7 by repeating the procedure of Example 5 except that the negative electrode of Comparative Example 3 was used.

Charge-Discharge Test

A charge-discharge test was performed on the bipolar test cells of Examples 3 to 5 and Comparative Examples 3 to 7 in an environment with a temperature of 20° C. The cell of Example 3 was charged to 4.3 V at 0.02 mA and was then discharge to 3.5 V at 0.02 mA. The cell of Example 4 was charged to 3.4 V at 0.02 mA and was then discharge to 2.5 V at 0.02 mA. The cell of Example 5 was reduced (charged) to 0.5 V at 0.02 mA and was then oxidized (discharged) to 3.0 V at 0.02 mA. The cell of Comparative Example 3 was charged to 5.0 V at 0.02 mA and was then discharged to 4.2 V at 0.02 mA. The cell of Comparative Example 4 was charged to 4.1 V at 0.02 mA and was then discharged to 3.2 V at 0.02 mA. The cell of Comparative Example 5 was charged to 3.5 V at 0.02 mA and was then discharged to 2.5 V at 0.02 mA. The cell of Comparative Example 6 was charged to 2.7 V at 0.02 mA and was then discharged to 1.5 V at 0.02 mA. The cell of Comparative Example 7 was reduced (charged) to 0.5 V at 0.02 mA and was then oxidized (discharged) to 3.0 V at 0.02 mA.

Results and Discussions

Figure 12:
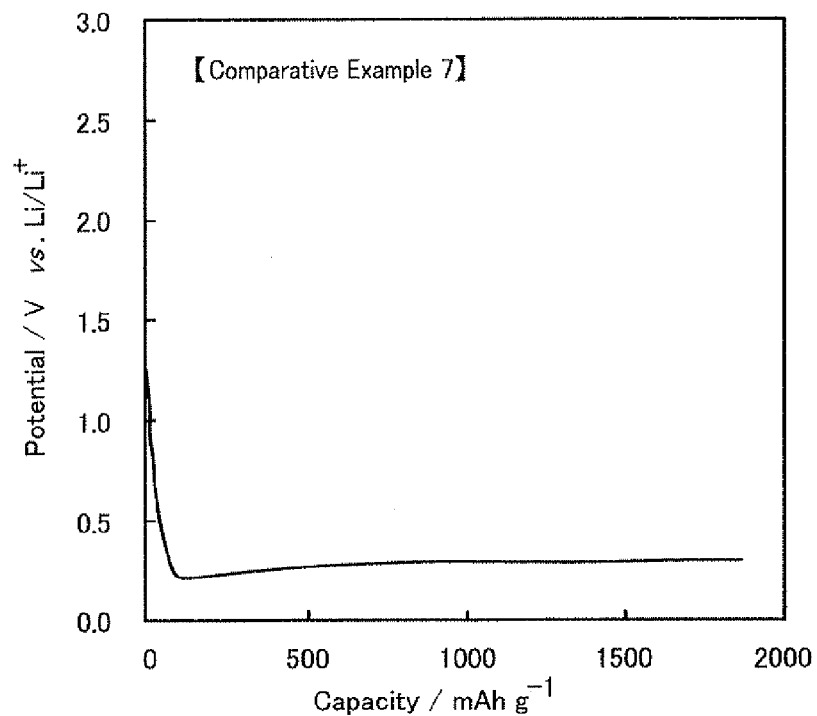
FIG. 12 shows a charge-discharge curve for Comparative Example 7.
Figure 13:
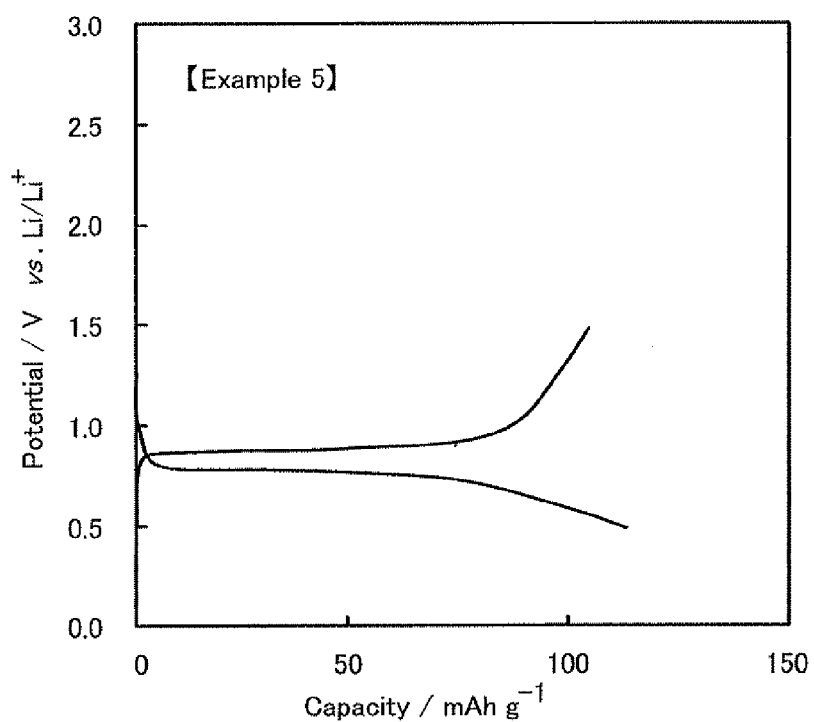
FIG. 13 shows a charge-discharge curve for Example 5.

FIG. 12 shows a charge-discharge curve for Comparative Example 7, and FIG. 13 shows a charge-discharge curve for Example 5. In addition, Table 2 summarizes the results of the charge-discharge test for the bipolar test cells of Examples 3 and 4 and Comparative Examples 3 to 6. Table 2 shows the positive electrode active materials, the negative electrode active materials, the collectors, the results of the operation, the full-charge and end-of-discharge voltages, and the battery voltages at a residual capacity SOC of 50%. As shown in FIG. 12, the cell of Comparative Example 7, which used an aluminum collector for a negative electrode containing graphite, exhibited a flat-potential plateau region around 0.27 V with respect to lithium metal during the reduction process, although no charge or discharge occurred thereafter. When the cell was dismantled after the charge-discharge test, the electrode was found to be corroded, which indicates that the alloying reaction of aluminum as a collector, rather than the charging of graphite as an active material, occurred. Similarly, as shown in Table 2, the cells of Comparative Examples 3 and 4, which used an aluminum metal collector and a negative electrode containing graphite as a negative electrode active material, did not operate as a battery. This demonstrates that an electrode including graphite as a negative electrode active material and aluminum as a collector corrodes and fails to operate reversibly because the alloying reaction between aluminum and lithium occurs at a potential higher than the charge-discharge reaction potential. Presumably, therefore, a negative electrode containing graphite does not operate as a battery when fabricated as a bipolar electrode by forming a negative electrode mixture layer and a positive electrode mixture layer on either side of an aluminum collector. In contrast, the cells of Comparative Examples 5 and 6, which used an aluminum metal collector and a negative electrode containing lithium titanate as a negative electrode active material, operated, although the respective voltages at a residual capacity SOC of 50% were 3.2 and 2.2 V, which were lower than those of Examples 3 and 4, i.e., 4.0 and 3.0 V. Thus, the cells of Examples 3 and 4 produced higher voltages than the cells of Comparative Examples 5 and 6. As shown in FIG. 13, additionally, the cell of Example 5, which used an aluminum collector for a negative electrode containing a layered composition, exhibited a flat-potential plateau region around 0.7 to 0.8 V with respect to lithium metal, indicating that it charges and discharges reversibly. This demonstrates that an electrode including aluminum as a collector and a layered composition as a negative electrode active material can operate reversibly without corrosion of the aluminum collector because the charge-discharge reaction occurs at a potential higher than the potential at which the alloying reaction between aluminum and lithium occurs, i.e., 0.27 V. Thus, the results demonstrate that a bipolar electrode fabricated using aluminum as a collector and a layered composition as a negative electrode active material can operate as a battery and provides a battery having a higher energy density than one including collectors of different materials for positive and negative electrodes (see FIGS. 3 to 5). The results also demonstrate that a layered composition can form a battery having a higher voltage than lithium titanate because of its lower potential with respect to lithium metal, thus providing a battery having a higher energy density.

as a binder and dispersing the mixture using an appropriate amount of N-methyl-2-pyrrolidone as a dispersant. The slurried mixture was uniformly applied to a 10 μm thick aluminum foil collector and was dried by heating to fabricate a coated sheet. The coated sheet was then pressed and punched to prepare a circular electrode having an area of 2.05 cm².

Fabrication of Bipolar Test Cell of Experimental Example 1

A nonaqueous electrolyte solution (ion-conducting medium) was prepared by adding lithium hexafluorophosphate to a concentration of 1 mol/L in a nonaqueous solvent containing a 1,2-difluoroethylene carbonate (hereinafter also referred to as "material A") as a cyclic halogenated carbonate and trifluoroethyl trifluoropropyl carbonate (hereinafter also referred to as "material B") as a linear halogenated carbonate in a volume ratio of 50:50. A bipolar test cell was fabricated by holding a separator (Tonen Tapyrus Co., Ltd.) impregnated with the above nonaqueous electrolyte solution between the coated electrode fabricated as above, serving as a working electrode, and a lithium metal foil (300 μm thick), serving as a counter electrode. The resulting cell is referred to as a bipolar test cell of Experimental Example 1.

Experimental Examples 2 to 4

A bipolar test cell was fabricated as a bipolar test cell of Experimental Example 2 by repeating the procedure of Experimental Example 1 except that the nonaqueous electrolyte solution of Experimental Example 1 was replaced by a nonaqueous electrolyte solution prepared by adding lithium hexafluorophosphate to a concentration of 1 mol/L in a nonaqueous solvent containing 1,2-difluoroethylene carbonate, trifluoroethyl trifluoropropyl carbonate, and an unfluorinated

TABLE 2

| | Positive Electrode Active Material | Negative Electrode Active Material | Collector | Result of Operation | Full-Charge Voltage and End-of-Discharge Voltages | SOC50% Voltage (V) |
| --- | --- | --- | --- | --- | --- | --- |
| Example 3 | Spinel $LiNi_{0.5}Mn_{1.5}O_4$ | Layered Structure | Al | Operated | 4.3 V-3.5 V | 4.0 V |
| Example 4 | Layered $LiNi_{0.8}Co_{0.15}Al_{0.05}O_2$ | Layered Structure | Al | Operated | 3.4 V-2.5 V | 3.0 V |
| Comparative Example 3 | Spinel $LiNi_{0.5}Mn_{1.5}O_4$ | Graphite | Al | Not Operated | — | — |
| Comparative Example 4 | Layered $LiNi_{0.8}Co_{0.15}Al_{0.05}O_2$ | Graphite | Al | Not Operated | — | — |
| Comparative Example 5 | Spinel $LiNi_{0.5}Mn_{1.5}O_4$ | Li Titanate $LiTi_5O_{12}$ | Al | Operated | 3.5 V-2.5 V | 3.2 V |
| Comparative Example 6 | Layered $LiNi_{0.8}Co_{0.15}Al_{0.05}O_2$ | Li Titanate $LiTi_5O_{12}$ | Al | Operated | 2.7 V-1.5 V | 2.2 V |

Next, specific examples of research on ion-conducting media for nonaqueous secondary batteries of the present invention will be described below as the Experimental Examples.

Fabrication of Coated Electrode

A nonaqueous secondary battery electrode was fabricated using the active material powder of Example 1. A slurried mixture was prepared by mixing 60.0% by mass of the lithium 2,6-naphthalenedicarboxylate of Example 1, 10.0% by mass of a conductive fiber, i.e., vapor-grown carbon fiber (VGCF), having a specific surface area of 13 m²/g and an average fiber length of 15 μm as a conductor, 20.0% by mass of conductive particles, i.e., carbon black, having a specific surface area of 225 m²/g and an average particle size of 25 nm as a conductor, and 10.0% by mass of polyvinylidene fluoride carbonate in a volume ratio of 40:40:20. The unfluorinated carbonate used herein was a mixture of ethylene carbonate (EC), dimethyl carbonate (DMC), and ethyl methyl carbonate (EMC) in a volume ratio of 30:40:30. In addition, a bipolar test cell was fabricated as a bipolar test cell of Experimental Example 3 by repeating the procedure of Experimental Example 2 except that the electrolyte solution of Experimental Example 2 was replaced by a nonaqueous electrolyte solution containing 1,2-difluoroethylene carbonate, trifluoroethyl trifluoropropyl carbonate, and the unfluorinated carbonate in a volume ratio of 30:30:40. In addition, a bipolar test cell was fabricated as a bipolar test cell of Experimental Example 4 by repeating the procedure of Experimental Example 2 except that the electrolyte solution of Experimental Example 2 was replaced by a nonaqueous electrolyte solution containing 1,2-difluoroethylene carbonate, trifluoroethyl trifluoropropyl carbonate, and the unfluorinated carbonate in a volume ratio of 20:20:60.

Experimental Examples 5 to 8

A bipolar test cell was fabricated as a bipolar test cell of Experimental Example 5 by repeating the procedure of Experimental Example 1 except that the lithium 2,6-naphthaledicarboxylate used as an electrode active material in Experimental Example 1 was replaced by the lithium 4,4'-biphenyldicarboxylate of Example 2. In addition, a bipolar test cell was fabricated as a bipolar test cell of Experimental Example 6 by repeating the procedure of Experimental Example 5 except that the nonaqueous electrolyte solution of Experimental Example 5 was replaced by the same nonaqueous electrolyte solution as used in Experimental Example 2, i.e., a nonaqueous electrolyte solution containing 1,2-difluoroethylene carbonate, trifluoroethyl trifluoropropyl carbonate, and the unfluorinated carbonate in a volume ratio of 40:40:20. In addition, a bipolar test cell was fabricated as a bipolar test cell of Experimental Example 7 by repeating the procedure of Experimental Example 6 except that the electrolyte solution of Experimental Example 6 was replaced by a nonaqueous electrolyte solution containing 1,2-difluoroethylene carbonate, trifluoroethyl trifluoropropyl carbonate, and the unfluorinated carbonate in a volume ratio of 30:30:40. In addition, a bipolar test cell was fabricated as a bipolar test cell of Experimental Example 8 by repeating the procedure of Experimental Example 6 except that the electrolyte solution of Experimental Example 6 was replaced by a nonaqueous electrolyte solution containing 1,2-difluoroethylene carbonate, trifluoroethyl trifluoropropyl carbonate, and the unfluorinated carbonate in a volume ratio of 20:20:60.

Nonaqueous Secondary Battery of Experimental Example 9

A slurried mixture was prepared by mixing 85.0% by mass of $LiNi_{0.5}Mn_{1.5}O_4$ as a positive electrode active material, 10.0% by mass of carbon black as a conductor, and 10.0% by mass of polyvinylidene fluoride as a binder and dispersing the mixture using an appropriate amount of N-methyl-2-pyrrolidone as a dispersant. The slurried mixture was uniformly applied to a 10 μm thick aluminum foil collector and was dried by heating to fabricate a coated sheet. The coated sheet was then pressed and punched to prepare a circular electrode having an area of 2.05 cm$^2$. The lithium 2,6-naphthaleledicarboxylate electrode shown in Experimental Example 1 was used as a negative electrode active material. A nonaqueous secondary battery of Experimental Example 9 was fabricated by holding a separator (Toners Tapyrus Co., Ltd.) impregnated with the same nonaqueous electrolyte solution as used in Experimental Example 1 between the positive electrode and the negative electrode.

A nonaqueous secondary battery was fabricated as a nonaqueous secondary battery of Experimental Example 10 by repeating the procedure of Example 9 except that the lithium 2,6-naphthaleledicarboxylate electrode of Example 9 was replaced by the lithium 4,4'-biphenyldicarboxylate electrode of Experimental Example 5.

Experimental Examples 11 and 12

A bipolar test cell was fabricated as a bipolar test cell of Experimental Example 11 by repeating the procedure of Experimental Example 2 except that the electrolyte solution of Experimental Example 2 was replaced by a nonaqueous electrolyte solution containing 1,2-difluoroethylene carbonate, trifluoroethyl trifluoropropyl carbonate, and the unfluorinated carbonate in a volume ratio of 10:10:80. In addition, a bipolar test cell was fabricated as a bipolar test cell of Experimental Example 11 by repeating the procedure of Experimental Example 2 except that the electrolyte solution of Experimental Example 2 was replaced by a nonaqueous electrolyte solution containing 1,2-difluoroethylene carbonate, trifluoroethyl trifluoropropyl carbonate, and the unfluorinated carbonate in a volume ratio of 0:0:100, i.e., a nonaqueous electrolyte solution containing 100% by volume of the unfluorinated carbonate.

Experimental Examples 13 and 14

A bipolar test cell was fabricated as a bipolar test cell of Experimental Example 13 by repeating the procedure of Experimental Example 5 except that the electrolyte solution of Experimental Example 5 was replaced by a nonaqueous electrolyte solution containing 1,2-difluoroethylene carbonate, trifluoroethyl trifluoropropyl carbonate, and the unfluorinated carbonate in a volume ratio of 10:10:80. In addition, a bipolar test cell was fabricated as a bipolar test cell of Experimental Example 14 by repeating the procedure of Experimental Example 5 except that the electrolyte solution of Experimental Example 5 was replaced by a nonaqueous electrolyte solution containing 1,2-difluoroethylene carbonate, trifluoroethyl trifluoropropyl carbonate, and the unfluorinated carbonate in a volume ratio of 0:0:100, i.e., a nonaqueous electrolyte solution containing 100% by volume of the unfluorinated carbonate.

Experimental Examples 15 and 16

A nonaqueous secondary battery was fabricated as a nonaqueous secondary battery of Experimental Example 15 by repeating the procedure of Experimental Example 9 except that the electrolyte solution of Experimental Example 9 was replaced by a nonaqueous electrolyte solution containing ethylene carbonate (EC), dimethyl carbonate (DMC), and ethyl methyl carbonate (EMC) in a volume ratio of 30:40:30, i.e., a nonaqueous electrolyte solution containing 100% by volume of the unfluorinated carbonate. In addition, a nonaqueous secondary battery was fabricated as a nonaqueous secondary battery of Experimental Example 16 by repeating the procedure of Experimental Example 10 except that the electrolyte solution of Experimental Example 10 was replaced by a nonaqueous electrolyte solution containing 100% by volume of the unfluorinated carbonate.

Experimental Examples 17 and 18

A bipolar test cell was fabricated as a bipolar test cell of Experimental Example 17 by repeating the procedure of Experimental Example 1 except that the electrolyte solution of Experimental Example 1 was replaced by a nonaqueous electrolyte solution prepared by adding lithium hexafluorophosphate to a concentration of 1 mol/L in a nonaqueous solvent containing fluoroethylene carbonate (hereinafter also referred to as "material C") and ethyl methyl carbonate (EMC) in a volume ratio of 50:50. In addition, a bipolar test cell was fabricated as a bipolar test cell of Experimental Example 18 by repeating the procedure of Experimental Example 5 except that the electrolyte solution of Experimental Example 5 was replaced by a nonaqueous electrolyte solution prepared by adding lithium hexafluorophosphate to a concentration of 1 mol/L in a nonaqueous solvent containing fluoroethylene carbonate and ethyl methyl carbonate (EMC) in a volume ratio of 50:50.

Charge-Discharge Test

In an environment with a temperature of 20° C., the cells of Experimental Examples 1 to 18 described above were charged to 4.2 V at 0.02 mA and were then discharged to 3.2 V at 0.02 mA. This charge-discharge operation was repeated for ten cycles, and the percentage of the discharge capacity for the tenth cycle to the discharge capacity for the first cycle was determined as the capacity retention (%).

Results and Discussions

Figure 14:
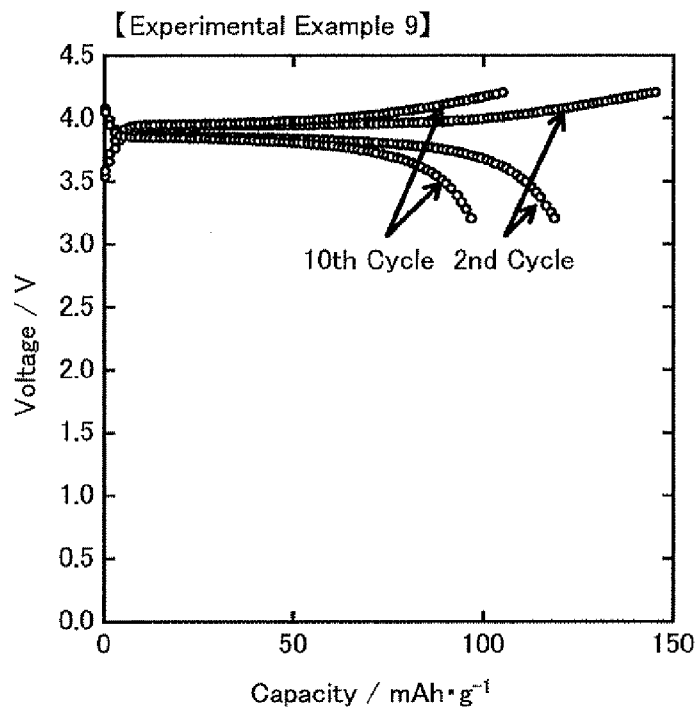
FIG. 14 shows charge-discharge curves for the second and tenth cycles in Experimental Example 9.
Figure 15:
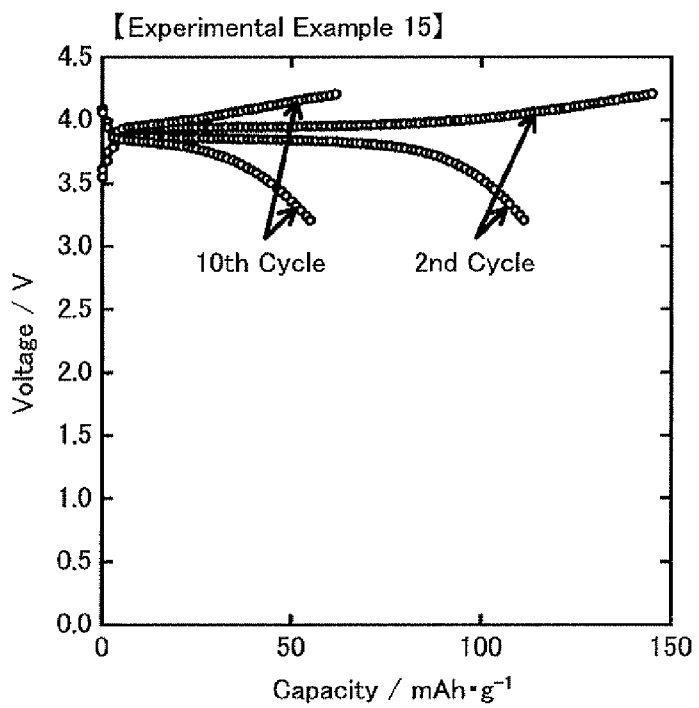
FIG. 15 shows charge-discharge curves for the second and tenth cycles in Experimental Example 15.
Figure 16:
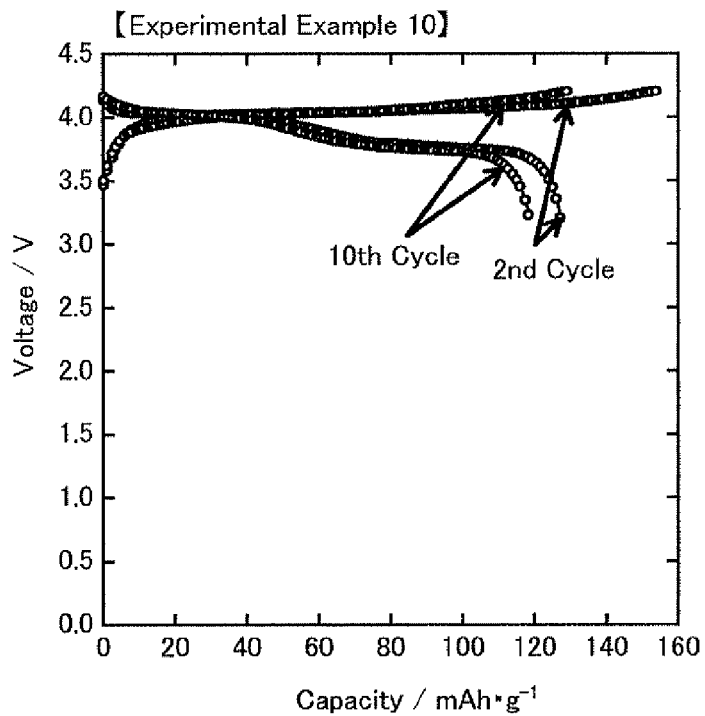
FIG. 16 shows charge-discharge curves for the second and tenth cycles in Experimental Example 10.
Figure 17:
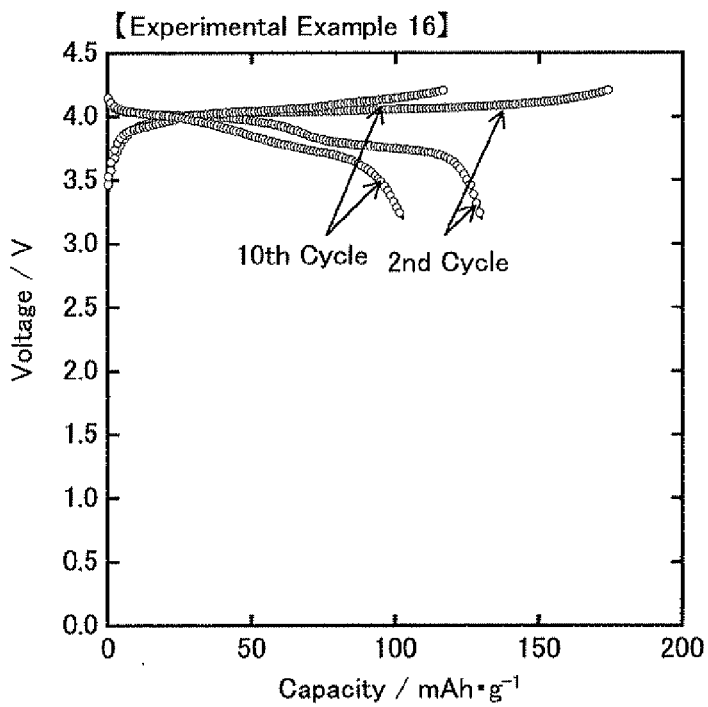
FIG. 17 shows charge-discharge curves for the second and tenth cycles in Experimental Example 16.
Figure 18:
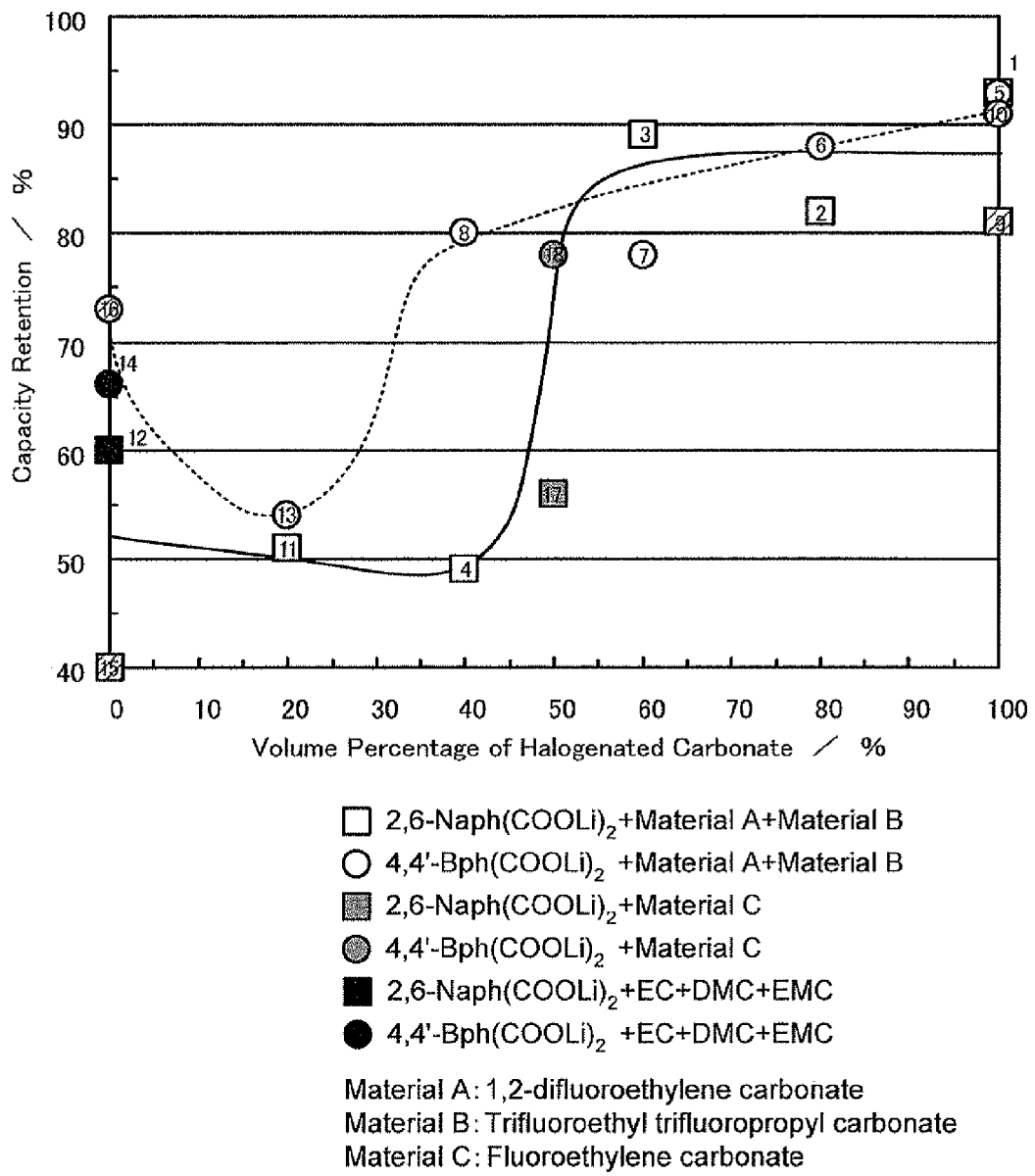
FIG. 18 is an illustration showing the relationship between the volume percentage of a halogenated carbonate and capacity retention.

Table 3 summarizes the compositions of the bipolar test cells and nonaqueous secondary batteries of Experimental Examples 1 to 18 and the results of the charge-discharge test. Table 3 shows the positive electrode active materials, the negative electrode active materials, the volume ratios of the nonaqueous electrolyte solutions, the volume percentages (%) of the halogenated carbonates contained in the nonaqueous electrolyte solutions, and the capacity retentions (%) for the tenth cycle. In addition, FIG. 14 shows charge-discharge curves for the second and tenth cycles in Experimental Example 9, FIG. 15 shows charge-discharge curves for the second and tenth cycles in Experimental Example 15, FIG. 16 shows charge-discharge curves for the second and tenth cycles in Experimental Example 10, and FIG. 17 shows charge-discharge curves for the second and tenth cycles in Experimental Example 16. In addition, FIG. 18 is an illustration showing the relationship between the volume percentage of the halogenated carbonates contained in the nonaqueous electrolyte solutions and the capacity retention.

equal proportions. It is known that trifluoroethyl trifluoropropyl carbonate is not readily decomposed in the potential range researched, i.e., 0.5 to 1.5 V, and no plateau due to decomposition of trifluoroethyl trifluoropropyl carbonate is found when, for example, a graphite electrode is used (J. Electrochem. Soc., 157, A707-A712, 2010). Probably, therefore, during initial absorption of lithium into the lithium 2,6-naphthaleledicarboxylate or lithium 4,4'-biphenyldicarboxylate electrode, 1,2-difluoroethylene carbonate is reduced to form lithium fluoride, which stabilizes the interface between the electrode and the electrolyte solution to prevent further decomposition of the electrolyte solution, thus improving the cyclability.

In addition, the results shown in Table 3, Experimental Examples 9 and 15, and FIGS. 14 and 15 demonstrate that a battery including a $LiNi_{0.5}Mn_{1.5}O_4$ positive electrode and a lithium 2,6-naphthaleledicarboxylate negative electrode provides a higher capacity retention if the nonaqueous electrolyte solution contains a halogenated carbonate in an amount of 60% to 100% by volume of the total amount of nonaqueous electrolyte solution. The results for these experimental examples also demonstrate that a nonaqueous secondary battery provides a higher capacity retention if 1,2-difluoroethylene carbonate or trifluoroethyl trifluoropropyl carbonate is contained in an amount of 30% to 50% by volume of the total amount of nonaqueous electrolyte solution. In addition, the results shown in Table 3, Experimental Examples 10 and 16, and FIGS. 16 and 17 demonstrate that a battery including a

TABLE 3

| | Positive Electrode[1] | Negative Electrode[1] | Material A[2] (vol %) | Material B[3] (vol %) | Material C[4] (vol %) | Non halogen Solvents[5] | Halogen Percentages[5] | Capacity Retention[6] |
|---|---|---|---|---|---|---|---|---|
| Experimental Example 1 | 2,6-Naph | Metallic Li | 50 | 50 | 0 | 0 | 100 | 93 |
| Experimental Example 2 | 2,6-Naph | Metallic Li | 40 | 40 | 0 | 20 | 80 | 82 |
| Experimental Example 3 | 2,6-Naph | Metallic Li | 30 | 30 | 0 | 40 | 60 | 89 |
| Experimental Example 4 | 2,6-Naph | Metallic Li | 20 | 20 | 0 | 60 | 40 | 49 |
| Experimental Example 5 | 4,4-Bph | Metallic Li | 50 | 50 | 0 | 0 | 100 | 93 |
| Experimental Example 6 | 4,4-Bph | Metallic Li | 40 | 40 | 0 | 20 | 80 | 88 |
| Experimental Example 7 | 4,4-Bph | Metallic Li | 30 | 30 | 0 | 40 | 60 | 78 |
| Experimental Example 8 | 4,4-Bph | Metallic Li | 20 | 20 | 0 | 60 | 40 | 80 |
| Experimental Example 9 | LiNiMnO | 2,6-Naph | 50 | 50 | 0 | 0 | 100 | 81 |
| Experimental Example 10 | LiNiMnO | 4,4-Bph | 50 | 50 | 0 | 0 | 100 | 91 |
| Experimental Example 11 | 2,6-Naph | Metallic Li | 10 | 10 | 0 | 80 | 20 | 51 |
| Experimental Example 12 | 2,6-Naph | Metallic Li | 0 | 0 | 0 | 100 | 0 | 60 |
| Experimental Example 13 | 4,4-Bph | Metallic Li | 10 | 10 | 0 | 80 | 20 | 54 |
| Experimental Example 14 | 4,4-Bph | Metallic Li | 0 | 0 | 0 | 100 | 0 | 66 |
| Experimental Example 15 | LiNiMnO | 2,6-Naph | 0 | 0 | 0 | 100 | 0 | 40 |
| Experimental Example 16 | LiNiMnO | 4,4-Bph | 0 | 0 | 0 | 100 | 0 | 73 |
| Experimental Example 17 | 2,6-Naph | Metallic Li | 0 | 0 | 50 | 50 | 50 | 56 |
| Experimental Example 18 | 4,4-Bph | Metallic Li | 0 | 0 | 50 | 50 | 50 | 78 |

[1] 2,6-Naph: Lithium 2,6-naphthaleledicarboxylate
4,4-Bph: Lithium 4,4'-biphenyldicarboxylate
LiNiMnO: $LiNi_{0.5}Mn_{1.5}O_4$
[2] Material A: 1,2-difluoroethylene carbonate
[3] Material B: Trifluoroethyl trifluoropropyl carbonate
[4] Material C: Fluoroethylene carbonate
[5] Non-halogen Solvent: Mixture of Ethylene carbonate (EC), dimethyl carbonate (DMC) and ethyl methyl carbonate (EMC), mixed in volume ratio of EC:DMC:EMC = 30:40:30
[6] Capacity Retention (%) in 10th cycle to capacity in 1st cycle As shown in Table 3, Experimental Examples 1 to 18 demonstrate that a nonaqueous electrolyte solution containing a halogenated carbonate, such as 1,2-difluoroethylene carbonate, trifluoroethyl trifluoropropyl carbonate, or fluoroethylene carbonate, generally has the tendency to provide a high capacity retention. In particular, for example, the cells and batteries of Experimental Examples 1 to 3, 5 to 10, and 18 exhibited extremely high capacity retentions. In the Experimental Examples herein, 1,2-difluoroethylene carbonate and trifluoroethyl trifluoropropyl carbonate were contained in $LiNi_{0.5}Mn_{1.5}O_4$ positive electrode and a lithium 4,4'-biphenyldicarboxylate negative electrode provides a higher capacity retention if a halogenated carbonate is contained in an amount of 40% to 100% by volume of the total amount of nonaqueous electrolyte solution. The results for these experimental examples also demonstrate that a nonaqueous secondary battery provides a higher capacity retention if 1,2-difluoroethylene carbonate or trifluoroethyl trifluoropropyl carbonate is contained in an amount of 20% to 50% by volume of the total amount of nonaqueous electrolyte solution.

The results further demonstrate that a nonaqueous secondary battery provides a higher capacity retention if 1,2-difluoroethylene carbonate, which is a cyclic halogenated carbonate, and trifluoroethyl trifluoropropyl carbonate, which is a linear halogenated carbonate, are contained. In addition, the measurement results for Experimental Examples 17 and 18 demonstrate that an electrolyte solution containing 50% by volume of fluoroethylene carbonate as a solvent provides high capacity retention. It should be noted that the same advantage will be provided by a polymer gel electrolyte containing a halogenated carbonate such as 1,2-difluoroethylene carbonate, trifluoroethyl trifluoropropyl carbonate, or fluoroethylene carbonate as an ion-conducting solvent that conducts alkali metal ions.

The present application claims priority to Japanese Patent Application No. 2010-236765 filed on Oct. 21, 2010 and Japanese Patent Application No. 2011-115093 filed on May 23, 2011, the entire contents of which are incorporated herein by reference.

Industrial Applicability

The present invention is applicable to the battery industry.

The invention claimed is:

1. A nonaqueous secondary battery electrode containing, as an electrode active material, a layered composition including organic backbone layers containing an aromatic compound that is a dicarboxylic acid anion having two or more aromatic ring structures and alkali metal element layers containing an alkali metal element coordinated to oxygen contained in the carboxylic acid anion to form a backbone.

2. The nonaqueous secondary battery electrode according to claim 1, wherein the layered composition is formed in layers by π-electron interaction of the aromatic compound and has a monoclinic crystal structure belonging to the space group $P2_1/c$.

3. The nonaqueous secondary battery electrode according to claim 1, wherein the layered composition has a structure of formula (1), where four oxygen atoms from different dicarboxylic acid anions form four coordination bonds with the alkali metal element:

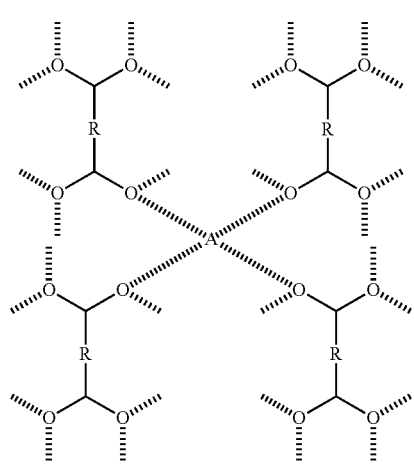

Formula (1)

where:
each R has two or more aromatic ring structures, and two or more of Rs may be the same, or one or more of Rs may be different; and
A is an alkali metal element.

4. The nonaqueous secondary battery electrode according to any one of claim 1, wherein the aromatic compound contained in the organic backbone layers has a structure represented by formula (2):

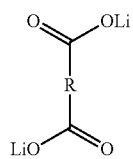

Formula (2)

where R has two or more aromatic ring structures.

5. The nonaqueous secondary battery electrode according to claim 1, wherein the aromatic compound contained in the organic backbone layers is one or more of aromatic compounds of formulas (3) to (5):

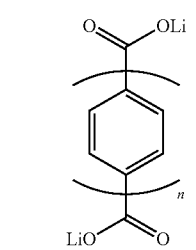

Formula (3)

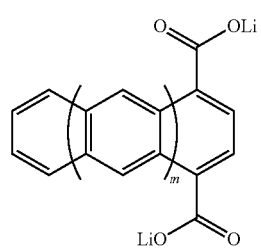

Formula (4)

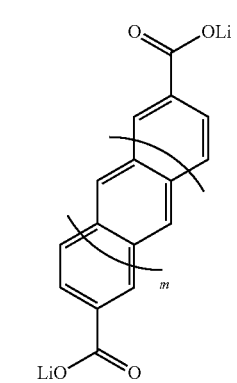

Formula (5)

where:
n is an integer of 2 to 5,
m is an integer of 0 to 3, and
the aromatic compounds may have a substituent or a heteroatom in the structures thereof.

6. The nonaqueous secondary battery electrode according to claim 1, wherein the aromatic compound contained in the organic backbone layers has the two carboxylic acid anions of the dicarboxylic acid anion bonded to diagonally opposite positions of the aromatic ring structures.

7. The nonaqueous secondary battery electrode according to claim 1, wherein the alkali metal element contained in the alkali metal element layers is Li.

8. The nonaqueous secondary battery electrode according to claim 1, wherein the layered composition is a negative electrode active material.

9. The nonaqueous secondary battery electrode according to claim 1, wherein the layered composition is provided on an aluminum metal collector.

10. The nonaqueous secondary battery electrode according to claim 1, comprising:
   a positive electrode mixture containing a positive electrode active material that absorbs and releases an alkali metal;
   a negative electrode mixture containing the layered composition as a negative electrode active material that absorbs and releases the alkali metal; and
   a collector having the positive electrode mixture provided on one side thereof and the negative electrode mixture provided on an opposing side thereof and comprising a collector metal that dissolves at a potential lower than the redox potential of the positive electrode active material and that undergoes an alloying reaction with the alkali metal at a potential higher than the redox potential of the negative electrode active material.

11. The nonaqueous secondary battery electrode according to claim 10, wherein the collector metal is aluminum metal.

12. The nonaqueous secondary battery electrode according to claim 10, wherein the positive electrode active material contained in the positive electrode mixture is at least one of a positive electrode active material having a spinel structure represented by the general formula $LiNi_xMn_{2-x}O_4$ (where $0 \leq x \leq 0.5$) and a positive electrode active material having a layered structure represented by the general formula $LiNi_{1-y}M_yO_2$ (where $0 \leq y \leq 0.5$, and M is one or more selected from Mg, Ti, Cr, Fe, Co, Cu, Zn, Al, Ge, and Sn).

13. The nonaqueous secondary battery electrode according to claim 10, wherein the average charge-discharge potential difference between the positive electrode side where the positive electrode mixture is provided and the negative electrode side where the negative electrode mixture is provided is 4.0 V or more.

14. A nonaqueous secondary battery comprising:
   the nonaqueous secondary battery electrode according to claim 1; and
   an ion-conducting medium that conducts alkali metal ions.

15. The nonaqueous secondary battery according to claim 14, wherein the ion-conducting medium contains a halogenated carbonate.

16. The nonaqueous secondary battery according to claim 14, wherein the ion-conducting medium contains a cyclic halogenated carbonate and a linear halogenated carbonate.

17. The nonaqueous secondary battery according to claim 14,
   wherein the layered composition contained as an electrode active material in the nonaqueous secondary battery electrode includes organic backbone layers having a fused polycyclic structure including two or more fused aromatic rings, and
   wherein the ion-conducting medium contains a halogenated carbonate in an amount of 60% to 100% by volume of the total amount of ion-conducting medium.

18. The nonaqueous secondary battery according to claim 14,
   wherein the layered composition contained as an electrode active material in the nonaqueous secondary battery electrode includes organic backbone layers having a non-fused polycyclic structure including two or more linked aromatic rings, and
   wherein the ion-conducting medium contains a halogenated carbonate in an amount of 40% to 100% by volume of the total amount of ion-conducting medium.

19. An assembled battery comprising a plurality of connected nonaqueous secondary batteries according to claim 14.

* * * * *